(12) United States Patent
Matthiesen et al.

(10) Patent No.: US 11,129,559 B2
(45) Date of Patent: Sep. 28, 2021

(54) FILTERING DEVICE FOR RECORDING ELECTROPHYSIOLOGICAL SIGNALS

(71) Applicant: CathVision ApS, Copenhagen N (DK)

(72) Inventors: Mads Emil Matthiesen, Copenhagen K (DK); Sigge Nejst Larsen, Copenhagen N (DK); Victor Shadbolt, Mississauga (CA); Harold Wodlinger, Thornhill (CA)

(73) Assignee: CathVision ApS, Copenhagen N (DK)

( * ) Notice: Subject to any disclaimer, the term of this patent is extended or adjusted under 35 U.S.C. 154(b) by 221 days.

(21) Appl. No.: 16/341,717

(22) PCT Filed: Oct. 13, 2017

(86) PCT No.: PCT/EP2017/076206
§ 371 (c)(1),
(2) Date: Apr. 12, 2019

(87) PCT Pub. No.: WO2018/069507
PCT Pub. Date: Apr. 19, 2018

(65) Prior Publication Data
US 2020/0037914 A1    Feb. 6, 2020

(30) Foreign Application Priority Data

Oct. 13, 2016 (EP) .................................. 16193690

(51) Int. Cl.
*A61B 5/0428* (2006.01)
*A61B 5/042* (2006.01)
(Continued)

(52) U.S. Cl.
CPC .............. *A61B 5/304* (2021.01); *A61B 5/287* (2021.01); *A61B 18/1492* (2013.01);
(Continued)

(58) Field of Classification Search
USPC .................................................. 600/522, 523
See application file for complete search history.

(56) References Cited

U.S. PATENT DOCUMENTS

| 5,357,956 | A | 10/1994 | Nardella |
| 6,027,500 | A | 2/2000 | Buckles |

(Continued)

FOREIGN PATENT DOCUMENTS

| CA | 2359445 A1 | 4/2003 |
| EP | 2446814 A1 | 5/2012 |

(Continued)

OTHER PUBLICATIONS

International Search Report and Written Opinion of International Searching Authority for Application No. PCT/EP2017/076206, dated Dec. 12, 2017 (12 pages).

(Continued)

*Primary Examiner* — Erin M Piateski
(74) *Attorney, Agent, or Firm* — Nixon Peabody LLP

(57) ABSTRACT

A switchable filter device for use in a system for recording electro-physiological signals. The filter device includes a plurality of recording channels, the recording channels having an ablation recording channel. Each recording channel has a patient side terminal at a patient interface and a corresponding recording side terminal at a recording device interface. Each recording channel includes a first signal path with a first frequency dependent transmission characteristic having a first pass band, a second signal path with a second frequency dependent transmission characteristic different from the first frequency dependent transmission characteristic, the second frequency dependent transmission characteristic having a second pass band overlapping the first pass band, and switching devices operable to switch between the first signal path and the second signal path in response to a control signal indicative of a transient interference signal.

(Continued)

Preferably, switching from the second signal path to the first signal path is performed with a switching delay after termination of the transient interference signal.

25 Claims, 5 Drawing Sheets

(51) Int. Cl.

| | |
|---|---|
| *A61B 18/14* | (2006.01) |
| *A61B 5/304* | (2021.01) |
| *A61B 5/287* | (2021.01) |
| *A61B 18/00* | (2006.01) |
| *A61B 18/12* | (2006.01) |

(52) U.S. Cl.
CPC .............. *A61B 2018/00357* (2013.01); *A61B 2018/00577* (2013.01); *A61B 2018/00702* (2013.01); *A61B 2018/00839* (2013.01); *A61B 2018/1293* (2013.01)

(56) References Cited

U.S. PATENT DOCUMENTS

| | | | |
|---|---|---|---|
| 8,248,137 B2 | 8/2012 | Peuscher | |
| 2005/0119708 A1 | 6/2005 | Haefner | |
| 2006/0293603 A1 | 12/2006 | Strandberg | |
| 2007/0299352 A1* | 12/2007 | Harlev | A61B 5/6852 |
| | | | 600/509 |
| 2011/0190625 A1 | 8/2011 | Harley | |
| 2011/0227638 A1 | 9/2011 | Peuscher | |
| 2012/0109242 A1* | 5/2012 | Levin | A61B 5/304 |
| | | | 607/17 |
| 2013/0184600 A1 | 7/2013 | Tan | |
| 2014/0121548 A1 | 5/2014 | Lou | |
| 2014/0128722 A1* | 5/2014 | Schweitzer | G01R 33/5673 |
| | | | 600/411 |
| 2014/0364715 A1 | 12/2014 | Hauck | |
| 2015/0005585 A1 | 1/2015 | Xu | |
| 2015/0119690 A1* | 4/2015 | Deno | G01R 33/285 |
| | | | 600/411 |
| 2015/0297107 A1* | 10/2015 | Sullivan | A61B 5/24 |
| | | | 600/523 |
| 2015/0320481 A1* | 11/2015 | Cosman, Jr. | A61B 18/16 |
| | | | 606/35 |
| 2016/0166171 A1* | 6/2016 | Warner | A61B 5/304 |
| | | | 340/870.07 |
| 2016/0248434 A1 | 8/2016 | Govari | |
| 2017/0224244 A1 | 8/2017 | Kuwabara et al. | |
| 2018/0199976 A1* | 7/2018 | Fischer | A61B 18/02 |

FOREIGN PATENT DOCUMENTS

| | | | |
|---|---|---|---|
| EP | 2740403 A1 | 6/2014 | |
| JP | H11-332842 A | 12/1999 | |
| JP | 2011-072725 A | 4/2011 | |
| JP | 2012-090986 A | 5/2012 | |
| JP | 2016-524480 A | 8/2016 | |
| JP | 2016152624 A | 8/2016 | |
| WO | WO 2010/103542 A2 | 9/2010 | |
| WO | 2016024495 A1 | 2/2016 | |

OTHER PUBLICATIONS

International Search Report and Written Opinion of International Searching Authority for Application No. PCT/EP2016/057783, dated Jun. 17, 2016 (10 pages).

Stevenson, W. et al.; "Recording Techniques for Clinical Electrophysiology"; Journal of Cardiovascular Electrophysiology, vol. 16, No. 9, pp. 1017-1022; Sep. 1, 2005; XP055222320; ISSN: 1045-3873.

International Search Report and Written Opinion of International Searching Authority for Application No. PCT/EP2017/076208, dated Dec. 13, 2017 (11 pages).

Razzaq, N. et al.; "An Intelligent Adaptive Filter for Elimination of Power Line Interference From High Resolution Electrocardiogram"; IEEE Access, vol. 4, pp. 1676-1688; Mar. 31, 2016; XP011611726.

Yegui, X. et al.; "A new LMS-based Fourier analyzer in the presence of frequency mismatch and applications"; IEEE Transactions on Circuits and Systems Part I: Regular Papers, vol. 52, No. 1, pp. 230-245; Jan. 10, 2005; XP055355532.

U.S. Appl. No. 16/341,812, filed Apr. 12, 2019, Mads Emil Matthiesen, System for Adaptive Filtering of Cardiac Signals.

* cited by examiner

FILTERING DEVICE FOR RECORDING ELECTROPHYSIOLOGICAL SIGNALS

CROSS-REFERENCE TO RELATED APPLICATIONS

This application is a U.S. National Stage of International Application No. PCT/EP2017/076206, filed Oct. 13, 2017, which claims the benefit of European Patent Application No. 16193690.1, filed Oct. 13, 2016, both of which are incorporated herein by reference in their entireties.

The present invention relates in one aspect to a switchable filter device for use in a system for recording intracardiac electrophysiological signals and for providing radiofrequency (RF) ablation energy at intracardiac locations, the filter device comprising: a plurality of recording channels, the recording channels comprising an ablation recording channel, wherein each recording channel at a patient interface has a patient side terminal and at a recording device interface has a corresponding recording side terminal; an ablation input channel with an ablation input terminal and an ablation output terminal, wherein the ablation input channel is configured for transmitting a radiofrequency ablation signal from the ablation input terminal to the ablation output terminal. According to a further aspect, the present invention relates to a system for recording intracardiac electrophysiological signals and for providing radiofrequency ablation energy at intracardiac locations. According to a yet further aspect a filtering device and method for use in a system for recording of electrophysiological signals in the presence of transient interference signals.

BACKGROUND OF THE INVENTION

Intracardiac electrophysiological measurements are considered an important tool for understanding and treating cardiac problems, such as arrhythmia phenomena. Intracardiac measurements are obtained in so-called minimally invasive procedures using intracardiac catheters. Advanced equipment includes multiple electrode catheters having a plurality of electrodes that can be located inside the heart. Depending on the procedures to be performed, such catheters at their distal end are equipped with electrodes configured for picking up an electrophysiological potential at the respective location of the electrodes. The electrophysiological potentials are passed via electrical conductors from the distal end of the catheter to a connector interface at the proximal end of the catheter, and further to recording equipment for amplification, processing, display and storage of signals representative of the intracardiac electrophysiological potentials. The intracardiac electrophysiological signals are the observation of the intracardiac electrophysiological potentials as a function of time, wherein the intracardiac electrophysiological signals are measured by amplifying the potential difference between a first terminal and a second terminal, wherein at least the first terminal is connected to an electrode that is placed inside the heart. The obtained intracardiac signals may be further amplified/processed and/or digitized for display on a computer and/or storage on a digital storage medium.

By recording/mapping a plurality of electrophysiological signals from signal electrodes placed inside the heart, details about a pathological state relating to cardiac arrhythmia in an individual can be obtained and proper treatment, such as an ablation treatment, can be developed. The aspects of the recorded intracardiac signals to be studied include the presence or absence of characteristic features in a given signal, the periodicity and regularity of repetition of the signals, as well as the amplitude and morphology of the signals.

A major challenge in the recording of intracardiac electrophysiological signals is the interference from electrical noise sources, which is picked up by the highly sensitive apparatus. Amongst the main causes for such noise is in particular the prominent mains interference at around 50 Hz or around 60 Hz—depending on the local frequency standard for mains supply. Other sources of noise include internal amplifier noise, artefacts due to movement of the wiring used for recording, and electrode DC-offsets. The noise may include noise components common to all signals (common mode noise) and noise components that vary from signal to signal (differential mode noise).

Processing the signals e.g. by filtering at frequencies corresponding to the noise sources may suppress some of the noise. However, such filtering tends to affect the morphology of the signals and therefore has to be done with the utmost care. A useful system and method for processing signals from intracardiac catheters, in particular taking into account considerations of signal morphology, is for example disclosed in co-pending international patent application PCT/EP2016/057783, which is hereby incorporated by reference.

As mentioned above, a proper recording of intracardiac electrophysiological potentials is instrumental, if not indispensable, for performing ablation treatment in an intracardiac procedure, such as radiofrequency catheter ablation. Radiofrequency catheter ablation is a procedure in which tissue that is part of the electrical conduction system of the heart is scared (ablated) using the heat generated from alternating current applied to the tissue. Typical frequencies for radiofrequency ablation are above 300 kHz, usually in a range between 350 kHz and 600 kHz, or in a range between 400 kHz and 500 kHz, or at about 500 kHz. The applied radiofrequency energy is used to interrupt abnormal electrical pathways in cardiac tissue that are contributing to a cardiac arrhythmia.

Radiofrequency catheter ablation procedures may e.g. be indicated for cases of atrial fibrillation, recurrent atrial flutter, atrial tachycardia, multifocal atrial tachycardia, supraventricular tachycardia, and ventricular arrhythmia. The energy-emitting probe (electrode) is located at the distal end of a catheter which is placed into the heart. The relevant intracardiac locations to be scared may be identified in a mapping operation identifying regions of abnormal electrical activity. Once the relevant tissue has been identified, an ablation procedure is performed typically involving the "drawing-up" point-by-point one or more scar lines of ablated tissue. A high quality recording of intracardiac electrophysiological signals both prior to and during the actual ablation is therefore important for the treatment to succeed. Furthermore, a high quality recording of intracardiac electrophysiological signals is also important after the ablation has been performed, not the least for confirming the correct treatment.

However, the radiofrequency power introduced through the catheter into the patient for achieving ablation of tissue in the heart is several orders of magnitude larger than the electrophysiological signals to be recorded. The RF ablation power and the intracardiac electrophysiological signals may differ by a factor of 10,000, or even by a factor of 100,000 in amplitude. Furthermore, the interface between the ablation electrode and the tissue typically causes baseline drift, which can drive the electrophysiological signal to be recorded from the ablation electrode out of the amplifier's input range. Therefore filtering is typically required in order to be able to record intracardiac electrophysiological signals during ablation.

U.S. Pat. No. 6,027,500 describes a cardiac ablation system including an ablation catheter, a radiofrequency ablation device, a patient interface for acquiring intracardiac ECG signals, and a stimulator connected to the patient interface for providing pacing signals. The system according to U.S. Pat. No. 6,027,500 further includes a filter arranged between the catheter and the patient interface for suppressing the interference to the intracardiac electrophysiological signals by the RF ablation energy signal. However, solutions with a filter optimized for removing the ablation energy signal tend to compromise the quality of electrophysiological signal collected at times before or after ablation, e.g. because the RF ablation energy filter affects common mode rejection.

U.S. Pat. No. 5,357,956 discloses an apparatus and a method for monitoring endocardial signals during ablation. In this approach, a timing element operates a plurality of switches to selectively isolate, dampen, or interconnect various signal paths during plural repetitive non-overlapping ablation and quiescent intervals which alternate at a rate substantially above a Nyquist sampling rate. RF energy is delivered to the ablation site during the ablation intervals, whereas the local endocardial signal is measured during the quiescent intervals. However, such a solution involves a particular protocol for the delivery of the RF ablation energy in ablation intervals interrupted by so-called quiescent intervals. The solution thus imposes particular constraints on the ablation procedure and requires specialized control of both the ablation apparatus and the recording apparatus in a synchronized manner, thereby adding to the complexity of the set-up and compromising compatibility with existing ablation apparatus and electrophysiology monitoring set-ups.

Therefore there is a need for a system and method for recording low-noise intracardiac signals before, during, and after ablation, that is compatible with, or at least easily adaptable to, existing ablation equipment and that overcomes at least some of the above-mentioned problems of the prior art. Furthermore, there is a more general need for a system and method for ongoing recording of low-noise electrophysiological signals throughout cardiac procedures, i.e. in an environment where strong interfering signals may occur and perturb the quality of the collected electrophysiological signals in a persistent manner.

SUMMARY OF THE INVENTION

According to a broad aspect of the invention, a switchable filter device for use in a system for recording electrophysiological signals comprises a plurality of recording channels; wherein each recording channel has a patient side terminal at a patient interface and a corresponding recording side terminal at a recording device interface; wherein each recording channel comprises a first signal path with a first circuit configuration having a first frequency dependent transmission characteristic having a first pass band, a second signal path with a second circuit configuration having a second frequency dependent transmission characteristic different from the first frequency dependent transmission characteristic, the second frequency dependent transmission characteristic having a second pass band overlapping the first pass band; and wherein the switchable filter device further comprises switching devices operable to switch between the first signal path and the second signal path in response to a control signal indicative of a status of a transient interference signal.

Thereby, a filter device is achieved that allows for adapting the recording device to exceptional filtering requirements imposed by the presence of a transient interference signal that may exceed the electrophysiological signals to be recorded by orders of magnitude: the first signal path is adapted for coping with a standard recording environment in the absence of such strong transient interference signals; and the second signal path is adapted to coping with the exceptional situation of strong interference, due to the presence of a transient interference signal. Examples for such transient interference signals that may occur during intracardiac recording include defibrillation or the application of ablation energy as detailed further below by way of example. Since the adaptation is performed in response to a control signal indicating the status of the transient interference signal, the adaption may be performed in an automated manner. This reduces the complexity of parameters to be surveyed and controlled by an operator in charge of a cardiac intervention, thereby improving the reliability and safety of cardiac interventions.

Advantageously, the status information as indicated by the control signal includes "absence", "occurrence", "presence" and/or "termination" of the transient interference signal, wherein "occurrence" refers to the transition from "absence" to "presence", and wherein "termination" refers to the transition from "presence" to "absence". For the purpose of generating a representative control signal, the absence and presence of a transient interference signal, as well as the transition between the two, may be determined in any suitable way, e.g. by checking whether an input signal exceeds a pre-determined threshold amplitude (presence), or not (absence). For a given recording channel, the pre-determined threshold amplitude may, e.g. be determined as a specified input signal amplitude range. For example, interference may be detected from monitoring at least a DC-component of the unfiltered input signal and/or from monitoring a corresponding signal that is also affected by, and thus indicative of, the transient interference, such as a surface EKG-signal, a patient reference signal, etc. Such approaches may be particularly useful, e.g in the context of a defibrillation pulse applied to a patient while recording of electrophysiological signals is going on. Alternatively or in addition thereto, an activity signal may be provided by the apparatus generating the transient signal at the origin of the interference, and may thus be monitored for the purpose of developing a control signal indicative of the status of the transient interference signal. Further alternatively or in addition to the before-mentioned approaches a control signal indicative of the status of a transient interference signal may also be derived from a direct observation of the transient signal that is at the origin of the interference. Any such approaches of developing a control signal from an unfiltered electrophysiological signal, from a transient signal that may cause an interference, or from a status signal provided by a device generating such a transient signal that may cause an interference, is also particularly useful in the context of extremely delicate recording tasks, such as for the recording of intracardiac electrophysiological signals during an ablation procedure.

In response to the status information as indicated by the control signal, the switching means of the filter device may be operated to:

route the intracardiac electrophysiological signals so as to pass through the first signal path in the absence of any transient interference signal;

switch from the first signal path to the second signal path as soon as a transient interference signal occurs;

route the intracardiac electrophysiological signals so as to pass through the second signal path during the presence of the transient interference signal; and switch from the second signal path back to the first signal path after termination of the transient interference signal.

Preferably, switching from a circuit configuration of the second signal path to a circuit configuration of the first signal path is performed with a switching delay after termination of the transient interference signal. The switching delay starts with the event of termination of the transient interference signal as indicated by the control signal, and ends with the event that the circuit configuration of the first signal path is established again. The switching delay facilitates dealing with persistent artefacts induced in the intracardiac electrophysiological signals as a consequence of the strong interference and further allows for switching back from the harsh filtering as required during the presence of the transient interference, to the more lenient filtering in the absence thereof, without introducing prohibitively detrimental artefacts by the switching.

Advantageously according to some embodiments, the invention is particularly useful in the context of intracardiac ablation procedures that require constant monitoring of intracardiac electrophysiological signals in the vicinity of the location of intervention. By way of example, the usefulness of the invention is therefore described in the following with reference to such ablation procedures, where the transient interference signal stems from the radiofrequency power applied at intracardiac locations. The control signal may be generated by monitoring for a radiofrequency ablation signal, and generating a corresponding radiofrequency detection output indicative of the status of the interfering signal. In the case of detecting ablation, the switchable filter device may further comprise a radiofrequency detection device configured for receiving a radiofrequency ablation signal and providing a radiofrequency detection output in response to the presence of a radiofrequency ablation signal. A complementary output may then indicate the absence of a radiofrequency ablation signal.

A first aspect of the invention thus relates to a switchable filter device for use in a system for recording intracardiac electrophysiological signals and for providing radiofrequency ablation energy at intracardiac locations, the filter device comprising: a plurality of recording channels, the recording channels comprising at least one ablation recording channel, wherein each recording channel has a patient side terminal at a patient interface and a corresponding recording side terminal at a recording device interface; wherein the filter device further comprises a radiofrequency detection device configured for receiving a radiofrequency ablation signal and providing a radiofrequency detection output in response to the presence of a radiofrequency ablation signal (received at the detection device); and each recording channel comprises a first signal path with a first frequency dependent transmission characteristic having a first pass band, a second signal path with a second frequency dependent transmission characteristic different from the first frequency dependent transmission characteristic, the second frequency dependent transmission characteristic having a second pass band overlapping the first pass band, and switching devices operable to switch between the first signal path and the second signal path in response to the radiofrequency detection output.

The patient side terminal of the at least one ablation recording channel is adapted to be connected to an ablation electrode to be placed at an intracardiac ablation site, e.g. by means of an ablation catheter. The ablation recording channel is thus adapted for collecting intracardiac electrophysiological signals from the ablating electrode also during actual radiofrequency catheter ablation, i.e. while radiofrequency power is being applied to the ablating electrode. During operation, the ablation recording channel is therefore connected to the ablating electrode of an ablation catheter. When ablation energy is detected, additional filters are switched into the recording channels to allow signals to be recorded during ablation from all recording channels including the ablation recording channel, which is connected to collect electrophysiological signals from the ablating electrode. When ablation energy is not being applied, these filters are switched out of the recording channels in order to provide the maximum possible signal fidelity.

The radiofrequency ablation signal is indicative of the presence of a radiofrequency ablation power output by the ablation device/generator and/or indicative of the presence of a radiofrequency ablation power output at an ablation electrode of an intracardiac ablation catheter placed in a patient and connected to the filter device for recording of intracardiac electrophysiological signals. For example, the radiofrequency detection device may receive a radiofrequency ablation signal directly from an external ablation generator for detection purposes only, while the ablation generator is externally of the filter device connected to the ablation catheter for providing radiofrequency ablation energy to a patient. Alternatively, it is possible to avoid providing a dedicated connection from the ablation generator to the filter device by detecting the ablation signal directly from the ablating electrode connected to the ablation recording channel.

The radiofrequency ablation signal provided to the radiofrequency detection device may be the actual radiofrequency power provided by a radiofrequency ablation device/generator, or a fraction thereof. The fraction of the radiofrequency signal may be branched off the actual radiofrequency power provided by the radiofrequency ablation device/generator for detection purposes. The radiofrequency ablation signal may also be conceived to be a digital signal indicative of a radiofrequency ablation status with respect to the output of radiofrequency ablation power, e.g. to the patient. However, care has to be taken that such digital signal is generated with a sufficiently fast response time, in particular after ablation has started, in order to avoid an excessive lag between the presence of radiofrequency ablation power at the ablation electrode and switching of the signal paths to achieve a sufficiently continuous recording throughout an intracardiac ablation procedure.

The patient side terminals at the patient interface are adapted to be connected to one or more catheters for intracardiac procedures involving steps of recording intracardiac electrophysiological signals, applying stimulus to the heart, and/or modifying heart tissue by ablation. The patient side terminals at the patient interface are thus for collecting input in the form of electrophysiological signals from electrodes placed at intracardiac locations of a patient by means of a catheter. The signals collected at the patient side terminals are passed on to the respective recording channels for filtering before being presented as an output at the corresponding recording side terminals of the recording device interface. The electrophysiological signals collected at the patient side terminals are considered as unfiltered signals and the electrophysiological signals presented as output at the recording side terminals are considered as filtered signals.

At least one of the patient side terminals may collect a reference input in the form of an electrophysiological reference from an indifferent electrode arrangement placed on or in the patient. One of the recording channels is thus operable as a reference channel for providing an electrophysiological reference. A particularly advantageous location for taking an electrophysiological reference for intracardiac electrophysiological signals in the patient is e.g. the inferior vena cava.

The patient side terminals may further be adapted to provide output in the form of e.g. stimulation pulses destined for stimulation of the heart via the intracardiac electrodes of a connected catheter. The presence of a radiofrequency ablation signal is detected by the radiofrequency detection device. The RF-detection output provided by the RF-detection device indicates the presence (or absence) of interfering ablation-related artefacts and thus a need (or no need) to apply more aggressive filtering, before the intracardiac signal via the recording side terminal can be transmitted to an amplifying device for subsequent processing/recording. However, applying more aggressive filtering may affect signal quality. By automatically detecting whether or not a radiofrequency signal is present in the ablation channel, and feeding this information to a switchable filtering device, the aggressive filtering can be applied only when needed, e.g. when ablation energy is actually delivered, and switched off otherwise, i.e. when no ablation energy is delivered. According to some embodiments, the radiofrequency detection output may be a digital output allowing for discriminating between a first state and a second state complementary to the first state, wherein the first state causes passing the intracardiac signals through the first signal path, and wherein the second state causes passing the intracardiac signals through the second signal path. Depending on the logic applied by the switching device, the first state may be a logic "LOW" or "OFF" state, and the complementary second state a logic "HIGH" or "ON" state. Alternatively, the first state may be a logic "HIGH" or "ON" state, and the complementary second state a logic "LOW" or "OFF" state. However, different presentations of the radiofrequency detection output adapted for controlling the switching devices of the recording channels may be conceived.

The switching devices of the recording channels allow for switching between passing an intracardiac signal received at the patient side terminal of the channel to the corresponding recording side terminal either through the first signal path or through the second signal path. By switching on the filters adapted for suppressing radiofrequency ablation related artefacts only during ablation, the best possible signal quality is ensured at all times. The switching needs to happen quickly after the transmission of radiofrequency ablation power starts. For the sake of speed and also for the sake of usability, it is required that the switches are operated automatically. Therefore, a detection device is provided, which switches the radiofrequency ablation filters on very fast and switches the filters off again, after ablation has stopped. The switching devices may be operated in response to the radiofrequency-detection output as follows:

The first signal path is for passing the intracardiac signals in the absence of a radiofrequency ablation signal and the switches of the switching devices are set accordingly. Upon detection of the presence of a radiofrequency ablation signal, the radiofrequency detection device produces radiofrequency detection output causing the switching devices to set the switches of the channel so as to re-route the intracardiac signals through the second signal path. The second signal path is provided with filters adapted for suppressing interfering ablation-related artefacts, such as interference from the transmitted radiofrequency ablation power and/or base line drift, due to changes in the interface between the ablating electrode and the treated tissue. When the radiofrequency detection device has detected that the radiofrequency ablation power has been switched off, the switches are set back to pass the intracardiac signals through the first signal path.

The first and second signal paths have different frequency dependent transmission characteristics. The first signal path may thus be configured for an optimum signal quality in the absence of an RF-ablation signal, whereas the second signal path may be configured for filtering out RF-ablation related artefacts in order to obtain the most useful intracardiac signal for monitoring during ablation. The first and second pass bands should overlap such that both pass bands cover at least those frequencies where the majority of the frequency components of typical intracardiac signals are to be expected.

The second signal path imposes more aggressive filtering constraints as required under actual ablation, i.e. when radiofrequency ablation power is actually being applied at a given intracardiac location. For example, the second signal path may comprise a low pass filter and a high pass filter so as to form a band pass. Low pass filters may have to be adapted to attenuate ablation signals, which can be up to 300 V, down to less than 2 V in order to prevent saturation of subsequent amplifier circuits for the recording of intracardiac signals. Therefore, the low pass filters have a high frequency cut-off configured to effectively block signals at frequencies of the RF-ablation signal. However, this will typically also affect signal quality in respect to the suppression of other noise sources. In particular, when recording from multiple channels, the introduction of filter components may cause a decreased common mode rejection, because of variations between nominally identical filter components used in different recording channels. Such a difference may, e.g. cause an increased noise with a level of up to 100 µV or more. High pass filters are needed to avoid baseline drift that would bring the intracardiac signal out of the input range of a subsequent amplifier circuit for the recording of intracardiac signals. For example, it has been suggested that alterations in the electrode-tissue interface and/or built-up of charge may cause a drift in the base line DC-level. In any case during ablation considerable base line drift is typically observed, which can be quite steep. Therefore, the high pass filters have a low frequency cut-off configured to effectively suppress DC-components that otherwise would cause a base line drift. However, high pass filters have the same issue of decreased signal quality as the low pass filters mentioned above, in particular with respect to affecting the common mode rejection in a multiple channel recording set-up. Furthermore, high pass filters may increase signal recovery time for recording intracardiac signals after stimulation and defibrillation. Both low pass and high pass filters will decrease input impedance, which can also result in noise, if impedances of intracardiac electrodes are high and different from each other. The choice of the low and high frequency cut-off for the second signal path should thus be a compromise between, on the one hand, collecting a meaningful intracardiac signal and, on the other hand, suppressing undesired artefacts stemming from performing a radiofrequency catheter ablation procedure at intracardiac locations, such as base line drift and/or interference from the transmitted radiofrequency ablation power.

In the absence of an RF-ablation signal, the harsh filtering constraints of the second signal path may severely affect signal quality. The first pass-band is either broader than the second pass-band and/or filters less steeply by using fewer poles, thus lifting or at least relieving the harsh filtering constraints with respect to the second pass band, thus leading to an improved signal quality when the first signal path is chosen in the absence of radiofrequency ablation power. As mentioned above, the first and second pass bands should at least overlap the relevant range for intracardiac electrophysiological signals, where the majority of the frequency components of typical intracardiac signals are located or at least expected.

Advantageously according to some embodiments, the filter device further comprises an ablation input channel with an input terminal and an output terminal for passing the radiofrequency ablation power through the filter device, wherein the radiofrequency detection device communicates with the ablation channel for tapping off or otherwise deriving the radiofrequency ablation signal. Advantageously, the ablation input channel is configured for transmitting a radiofrequency ablation signal from the ablation input terminal to the ablation output terminal. Further advantageously, the ablation output terminal is connected at the patient interface to the patient side terminal of the ablation recording channel for delivering the radiofrequency ablation signal there through. Thereby, an improved integration of an ablation power output with the patient interface of the filter device is achieved. For integration, at least one of the patient side terminals is adapted to deliver ablation energy output in the form of a radiofrequency ablation signal to an ablation channel of a connected ablation catheter. Ablation catheters of different configurations are known to a person skilled in the art of radiofrequency catheter ablation, and the patient interface of the filtering device may be adapted to match such known configurations. The patient side terminal adapted for delivering ablation output receives the ablation energy in the form of a radiofrequency ablation signal via an ablation input channel from an ablation input terminal. The ablation input terminal is configured for receiving the radiofrequency ablation signal from an ablation signal generator. Ablation signal generators of different configurations are known to a person skilled in the art of radiofrequency catheter ablation, and the ablation input terminal of the filtering device may be adapted to match such known configurations.

Preferably according to some embodiments, the first pass-band is broader than the second pass-band. Advantageously according to some embodiments, a first pass band is broader than the second pass band, wherein a first low frequency cut-off of the first pass-band is less than a second low frequency cut-off of the second pass-band. Further advantageously according to some embodiments, a first pass band is broader than the second pass band, wherein a first high frequency cut-off of the first pass-band is larger than a second high frequency cut-off of the second pass-band.

Further Advantageously according to some embodiments, the first pass-band comprises the second pass-band. Thereby a configuration is achieved, where at least one of the frequency cut-offs, preferably both, of the first pass band are further away from the relevant range for intracardiac electrophysiological signals than the corresponding frequency cut-offs of the second pass band.

Further according to some embodiments, low pass filter components are only provided in the second signal path. Further according to some embodiments, high pass filter components are only provided in the second signal path. Preferably both low pass and high pass filter components are only provided in the second signal path. For example, the first signal path may be configured as a transmission line, or as a transmission line with unity gain buffers. In such embodiments switching between the first and second signal paths essentially amounts to switching the respective filter components of the second signal path on or off.

Further according to some embodiments of the filter device, a high frequency roll-off of the second frequency dependent transmission characteristic is steeper than a high frequency roll-off of the first frequency dependent transmission characteristic; and/or a low frequency roll-off of the second frequency dependent transmission characteristic is steeper than a low frequency roll-off of the first frequency dependent transmission characteristic. The first frequency dependent transmission characteristic has a first high frequency roll-off from the first pass band and the second frequency dependent transmission characteristic has a second high frequency roll-off from the second pass band, wherein the second high frequency roll-off from the second pass band is steeper than the first high frequency roll-off from the first pass band. Thereby a configuration is achieved, where at least one of the frequency cut-offs, preferably both, of the first pass band have less effect at the mains frequency, thus causing less degradation of common mode rejection than the corresponding frequency cut-offs of the second pass band.

Further according to some embodiments of the filtering device, a high frequency cut-off in the second signal path is between 5 kHz and 50 kHz, or between 5 kHz and 30 kHz, or between 6 kHz and 20 kHz, or between 7 kHz and 15 kHz. Values for the high-frequency cut-off are defined for the point where, with increasing frequency, attenuation drops below −3 db. With this selection of the high frequency cut-off for low pass filtering in the second signal path, radiofrequency ablation signals typically occurring at frequencies above 300 kHz, usually in the range between 400 kHz to 600 kHz, or at about 500 kHz, can be effectively blocked without affecting the recorded intracardiac signals too much, and in particular without compromising an efficient common mode rejection, e.g. for the suppression of mains interference, in the intracardiac electrophysiological signals recorded from multiple recording channels.

Further according to some embodiments of the filtering device, the low pass filter is designed to attenuate typical ablation frequencies, such as mentioned above, between −30 db and −60 db, preferably between −40 db and −50 db. This can be accomplished with several different filter configurations by selecting an appropriate combination of high frequency cut-off and roll-off steepness. Considering ablation frequencies in the range between 400 kHz and 600 kHz, or about 500 kHz, in one example the roll-off can be 40 dB per decade, and the high frequency cut-off can then be between 6 kHz and 15 kHz, preferably between 12 kHz and 15 kHz, or about 14 kHz. The roll-off can also be 60 dB per decade or more, and then the frequency cut-offs will be higher than those mentioned above. Preferably, the high frequency cut-off is in the range from 5 kHz or above 50 kHz, wherein a lower limit is for avoiding that the filter affects signal quality and an upper limit is determined by the required attenuation of the radiofrequency ablation signal in the recording channels for a given roll-off steepness. For a given required attenuation at a given ablation frequency, a larger high frequency cut-off would require a steeper roll-off in order to achieve the required attenuation. However, such a steeper roll-off may entail issues of increased circuit complexity, which may be require a larger footprint of the associated circuitry, may be more expensive to produce, and/or induce additional noise sources/signal variations, due to a larger number of electronic components involved.

Further according to some embodiments of the filtering device, a low frequency cut-off is 0.5 Hz or below, preferably 0.1 Hz or below, and most preferably 0.05 Hz or below. Values for the low frequency cut-off are defined for the point where, with decreasing frequency, attenuation drops below −3 db. With this selection of the high frequency cut-off for high pass filtering in the second signal path, DC-components that otherwise would cause a base line drift can be effectively suppressed, without affecting the recorded intracardiac signals too much, and in particular without compromising a subsequent efficient common mode rejection, e.g. for the suppression of mains interference, in the intracardiac electrophysiological signals recorded from multiple recording channels.

As mentioned above, switching between the first signal path and the second signal path in response to the radiofrequency detection output is performed by means of the switching devices receiving the detection output as a control signal. The switching devices may be configured to be operable according to advantageous embodiments as described in the following.

Further according to some embodiments of the filtering device, switching from the first signal path to the second signal path occurs within 100 ms, preferably within 10 ms, or even more preferably within 1 ms after start of a radiofrequency ablation cycle for providing radiofrequency ablation energy at an intracardiac location. Thereby, switching from the first signal path to the second signal path is required to occur quickly within an ablation start response time after a radiofrequency ablation signal has been applied at the ablation input terminal, wherein the ablation start response time does not exceed an upper limit of 100 ms, alternatively 50 ms, preferably 10 ms, alternatively 5 ms, or most preferably even 1 ms. A short response time is desired in order to avoid that the user experiences unacceptable lag between the event of switching on radiofrequency power for ablation causing the above-discussed ablation-related artefacts, and the availability of useful intracardiac electrophysiological signals for monitoring the heart activity during ablation. A lag caused by a response time of more than 100 ms is considered unacceptable to the user. A response time of below 100 ms is considered to lead to an acceptable lag. However, a response time of below 10 ms is preferred in order to provide a sufficiently steady observation of the intracardiac signals when starting a radiofrequency ablation pulse. Most preferably, a response time of 1 ms or below is provided in order to achieve an essentially unperturbed transition from monitoring/recording intracardiac signals in a period of without ablation to monitoring/recording in a period with ablation.

Further according to some embodiments of the filtering device, switching from the circuit configuration of the second signal path to the circuit configuration of the first signal path is performed with a switch-off delay. The switch-off delay is the period spanning from termination of a radiofrequency ablation signal applied at the ablation input terminal to completion of switching to the circuit configuration of the first signal path.

During radiofrequency ablation the intracardiac electrophysiological signals collected from intracardiac locations and provided at the patient side terminals tend to drift to an increased (positive or negative) DC-offset. This is in particular true for the intracardiac electrophysiological signals collected from the ablating electrode and electrodes probing the immediate vicinity of the ablation site. The respective intracardiac signals are kept within the dynamic range of a subsequent amplification circuitry by means of the high pass filters in the second signal path of the affected recording channels. After ablation has terminated, it will take some time before the respective intracardiac signal is back in range of the subsequent amplifying/recording device. To account for this relaxation, the control signal for switching the recording channels from the circuit configuration of the second signal path back to the circuit configuration of the first signal path is kept delayed. Preferably, a minimum delay for completing the transition from the circuit configuration of the second signal path to the circuit configuration of the first signal path is to be observed in particular before the high pass filter for suppressing radiofrequency ablation signals during ablation is fully switched off.

Advantageously, according to some embodiments, switching from the circuit configuration of the second signal path to the circuit configuration of the first signal path is completed with a switch-off delay of at least 0.1 s, at least 0.2 s, at least 0.5 s, or at least 1 s, or at least 2 s, or at least 5 s after termination of a radiofrequency ablation signal applied at the ablation input terminal.

Further according to some embodiments of the filtering device, the switching delay is at least 0.1 s, at least 0.2 s, at least 0.5 s, or at least 1 s, or at least 2 s, or at least 5 s after termination of a radiofrequency ablation signal applied at the ablation input terminal. Even if, or when, the intracardiac electrophysiological signal after ablation is within range, there may occur an abrupt DC jump to the natural offset, if the high pass filtering of the second signal path is switched off abruptly. This is avoided by requiring after termination of the radiofrequency ablation signal to perform a gradual transition from the circuit configuration of the second signal path to the circuit configuration of the first signal path over a minimum delay period, such as specified.

Further according to some embodiments of the filtering device, switching from the second signal path to the first signal path is performed via at least one intermediate stage, before entirely switching to the circuit configuration of the first signal path. During the at least one intermediate stage a high pass filter of the second signal path is referenced to an unfiltered signal line instead of being referenced to a common signal ground as during ablation. Preferably, at least a high pass filtering configuration is switched via at least one intermediate stage, during which the high pass filter of the second signal path is referenced to the unfiltered signal instead of being referenced to a common signal ground as during ablation. Upon expiry of the switching delay the circuit configuration of the respective recording channel is switched entirely to the first signal path. Thereby, an offset of the filtered intracardiac electrophysiological signal is driven to the offset of the unfiltered intracardiac electrophysiological signal, i.e. the offset as observed directly without filtering at the patient side terminal of the respective recording channel, thus avoiding or at least substantially reducing any artefacts in the filtered intracardiac signals as may be observed at the recording side terminal of the respective recording channel, due to an abrupt switching of the high pass filter.

Further according to some embodiments of the filtering device, switching from the second signal path to the first signal path is performed via at least two stages, before entirely switching to the circuit configuration of the first signal path: an initial relaxation stage with the high pass filter of the second signal path referenced to a common signal ground, thus maintaining the high pass configuration as during ablation; and, after the relaxation stage, a signal referenced stage with the high pass filter of the second signal path referenced to the unfiltered signal as described above. Thereby, the baseline offset of the unfiltered intracardiac electrophysiological signal is allowed to relax and/or settle after the radiofrequency ablation signal has been switched off, before the offset of the filtered intracardiac electrophysiological signal is actively driven to the offset of the unfiltered intracardiac electrophysiological signal as described above. Thereby suppression of signal path switching related artefacts may be further improved, e.g. by operating more reliably for a broader range of baseline offset voltages as observed upon switching off the radiofrequency ablation power.

Further according to some embodiments of the filtering device, switching from the second signal path to the first signal path is performed via at least two stages, before entirely switching to the circuit configuration of the first signal path: a primary signal referenced stage with the high pass filter of the second signal path referenced to the unfiltered signal; and, after the primary signal referenced stage, a secondary signal referenced stage with a secondary high pass filter configuration that is also referenced to the unfiltered signal, but wherein the secondary high pass filter has a low frequency cut-off above the low frequency cut-off of the primary signal referenced stage. By introducing an additional stage with an increased low-frequency cut-off as compared to the low frequency cut-off of the second signal path referenced to the unfiltered signal, the above-described process of driving the baseline offset to its natural offset may be further improved, e.g. by accelerating that process and/or bringing the offset of the filtered intracardiac signal in the recording channel closer to the offset of the unfiltered intracardiac electrophysiological signal, before entirely switching to the first signal path.

Advantageously, according to some embodiments, the gradual transition when switching from the second signal path to the first signal path is performed via at least three stages, before entirely switching to the circuit configuration of the first signal path: an initial relaxation stage with the high pass filter of the second signal path referenced to a common signal ground, thus maintaining the high pass configuration as during ablation; and, after the relaxation stage, a primary signal referenced stage with the high pass filter of the second signal path referenced to the unfiltered signal; and, after the primary signal tied stage, a secondary signal referenced stage with a secondary high pass filter configuration that is also referenced to the unfiltered signal, but wherein the secondary high pass filter has a low frequency cut-off above the low frequency cut-off of the primary signal tied stage. By coupling the above-mentioned embodiments using at least two stages in this particular sequence, their advantages of bringing the offset of the filtered intracardiac signal in the recording channel close to the offset of the unfiltered signal prior to switching are synergistically combined to achieve a yet further improved suppression of artefacts related to the switching of signal paths.

The stages of gradual switching should span the entire switch-off delay. For example, an initial stage may span the period between 0-1 s after ablation termination, a further stage may span the period between 1 s-2 s after ablation termination, and a yet further stage may span the period between 2 s-5 s after ablation termination. Further stages may be introduced in the process of switching after ablation termination from the second signal path back to the first signal path, as long as these intermediate stages are adapted for bringing the filtered signal closer to the unfiltered signal before the switch-off delay expires, i.e. before switching to the first signal is completed.

Further according to some embodiments of the filtering device, a subset of the plurality of recording channels is grouped together to form at least an ablation group, the ablation recording group comprising the ablation recording channel and at least a further recording channel.

Preferably, the filter configurations of the first and second signal paths in all recording channels within the ablation group are nominally identical. The term nominally identical is to be understood that the filter configurations are the same to within tolerances as determined by component tolerances in the respective filtering circuits. Further preferably, the switching devices of the recording channels of the ablation group are configured for synchronous operation in response to the radiofrequency detection output provided by the radiofrequency detection device.

The patient side terminal of the ablation recording channel is adapted to be connected to an ablation electrode to be placed at an intracardiac ablation site, e.g. by means of an ablation catheter. The patient side terminal of the at least one further recording channel is typically adapted and reserved to be connected to an indifferent electrode to be placed at a location on, or preferably in, a patient to provide an electrophysiological reference. This allows for the observation/construction of a unipolar intracardiac electrophysiological signal from the ablating electrode, with the improvements to signal quality, due to an ablation-dependent filtering, as discussed above. Alternatively, the further recording channel of the ablation group may be adapted to be connected to an intracardiac electrode to be placed at an intracardiac location adjacent to the ablation site. Typically, such an intracardiac electrode is arranged on the same catheter as and adjacent to the ablation electrode. This allows for the observation/construction of a bipolar intracardiac electrophysiological signal from the ablating electrode, with the improvements to signal quality, due to an ablation-dependent filtering, as discussed above. A nominally identical filter configuration in all recording channels of the ablation recording group allows for an efficient common mode noise reduction.

Depending on whether or not a radiofrequency ablation signal is delivered through the intracardiac terminal of the ablation recording channel, the filter configuration in all recording channels is switchable between first and second signal paths with respective first and second frequency dependent transmission characteristics, as described above. Synchronous switching between different signal paths in all channels ensures that the recording channels have the same respective filter configuration at essentially all times across the switching event.

Further according to some embodiments of the filtering device, the ablation group comprises a yet further recording channel, thereby allowing for the construction/observation of bipolar signals. The patient side terminal of the yet further recording channel is adapted to be connected to an intracardiac electrode adjacent to the intracardiac ablation electrode. The yet further recording channel may be referred to the further recording channel which is connectable to an electrophysiological reference of an indifferent electrode; This allows for the observation/construction of a further unipolar intracardiac electrophysiological signal from the yet further electrode with the same improvements in signal quality, due to an ablation-dependent filtering, as discussed above. Furthermore, bipolar signals may be observed by referring the ablation recording channel and the yet further recording channel to each other, or bipolar signals may be constructed from the respective unipolar electrophysiological signals.

Further according to some embodiments of the filtering device, an additional subset of the plurality of recording channels is grouped together to form an additional group, the additional recording group comprising at least two recording channels. Preferably, the filter configurations of the first and second signal paths in all recording channels within the additional group are nominally identical/the same. The term nominally identical is to be understood that the filter configurations are the same to within tolerances as determined by component tolerances in the respective filtering circuits. Further preferably, the switching devices of the recording channels of the additional group are configured for synchronous operation in response to the radiofrequency detection output provided by the radiofrequency detection device.

The additional group comprises preferably at least two recording channels, further preferably a multitude of recording channels. Thereby improved mains interference rejection may be achieved by suppressing common mode noise.

As in the ablation group, a nominally identical filter configuration is preferably provided in all recording channels of the additional group, and the switching between different respective signal paths is further preferably performed in a synchronized manner. The synchronized switches may be operated depending on the actual filter configurations of the first signal path, and in particular of the second signal path. The first signal path of the recording channels in the additional group is for passing the intracardiac signals in the absence of a radiofrequency ablation signal, whereas the second signal path is for passing the intracardiac signals during ablation. Typically, the switching from the first signal path to the second signal path (i.e. switching ablation filtering "ON") is performed synchronized with or at least within the same time frame as for the ablation group, i.e. as fast as possible upon detection of a radiofrequency ablation signal by the detection device in the ablation input channel. However, when switching the recording channels of the additional group after termination of the ablation from the second signal path back to the first signal path (i.e. switching ablation filtering "OFF"), it is typically not required to maintain the same switching-off delay as the for the ablation group if there is no high pass filter.

The recording channels of the additional group are not part of the subset of recording channels forming the ablation group. Furthermore, the additional group does not include an ablation recording channel. Therefore, the recording channels in the additional recording group typically receive intracardiac electrophysiological signals from a different electrophysiological noise and base line offset environment than the recording channels in the ablation recording group. The filter configuration of the recording channels in the additional recording group is therefore typically chosen to be different from that of the ablation recording group.

It turns out, that the recording channels of the additional group typically do not show the same level of base line drift, and therefore do not require the same level of high pass filtering as the recording channels of the ablation group. In fact, the high pass filtering may even be omitted for the recording channels of the additional group. The grouping of the recording channels into an ablation group and an additional group thus allows for a differentiated signal filtering approach optimized according to the actual noise environment. This may be achieved without compromising an efficient common mode rejection for at least those intracardiac electrophysiological signals that are not as severely affected during ablation as signals collected from the ablation site and its immediate surroundings. The ablation group recording channels can be configured for optimally dealing with radiofrequency related artefacts during ablation that are specific for the electrodes involved in or next to the ablation process, whereas the additional group's recording channels can be optimized for monitoring the intracardiac electrophysiological signals without having to take these ablation electrode specific constraints into account. Thereby, improved filtered intracardiac electrophysiological signals may be provided as output at the recording interface.

Typically, the additional recording channels are adapted for collecting intracardiac electrophysiological signals from electrodes at intracardiac locations. However, at least one of the recording channels is typically adapted for being connected to an indifferent electrode located on, or preferably in, a patient. The indifferent electrode is for providing an electrophysiological reference of the patient. The patient side terminals of the recording channels of the additional recording group are adapted to be connected to an intracardiac catheter, which is adapted for placing electrodes at intracardiac locations. The intracardiac electrodes to be connected to the additional recording group may be arranged on the same catheter as the intracardiac electrodes to be connected to the ablation recording group, or the electrodes may be arranged on different catheters. Just as in the ablation group, one of the recording channels in the additional group is typically reserved/adapted to be connected to an indifferent electrode to be placed at a location on, or preferably in, a patient to provide an electrophysiological reference. Preferably, the same electrophysiological reference is used for both the ablation group and the additional group. To that end, the electrophysiological reference may be received at the patient interface and split to be fed to the respective recording channels of the ablation group and of the additional group.

A second aspect of the invention relates to a system for recording intracardiac signals and for providing radiofrequency ablation energy at intracardiac locations, the system comprising: a switchable filter device according to any of the preceding claims; an ablation device coupled to the ablation input terminal for feeding a radiofrequency ablation signal to the ablation input channel; a differential amplifier stage coupled to the recording device interface of the switchable filter device for collecting the filtered electrophysiological signals from the recording channels, the differential amplifier stage being adapted to amplifying the filtered electrophysiological signals from the recording channels with respect to a signal reference to obtain respective amplified electrophysiological signals; and a processor device adapted to providing a (real time) output of intracardiac data based on the amplified electrophysiological signals. Most preferably, the output is provided as a real time output so as to provide immediate feedback about the current status of the heart under treatment to the user performing intracardiac procedures.

The system allows for recording of intracardiac electrophysiological signals during intracardiac radiofrequency ablation procedures with improved filtering. This is achieved by a reconfigurable filter design that is automatically tailored according to the presence or absence of a radiofrequency ablation signal, and the resulting noise conditions as discussed herein. The improved filtering ensures a sublime signal quality at all times, including when a radiofrequency ablation signal is actually applied through an ablation electrode at an intracardiac location, and after the radiofrequency ablation signal has been switched off. This allows for continuous intracardiac electrophysiological monitoring and provides immediate feedback to the practitioner/user throughout the entire radiofrequency catheter ablation procedure without discernible lag and/or dead times for the observation. Thereby, the switchable filtering device in combination with the ablation device, and devices for amplification/recording adapted for real time presentation of intracardiac electrophysiological signals synergistically improve the responsiveness and ease of use of the system, and thus synergistically improve the precision and quality of intracardiac radiofrequency ablation procedures performed with such a system that in this way is adapted for real time presentation.

Further according to some embodiments of the system, the switchable filtering device has recording channels that are grouped into an ablation group and an additional group as discussed above. Thereby the advantages of the filtering device with grouped recording channels as discussed above are utilized for the improvement of intracardiac radiofrequency ablation procedures performed using the system.

Advantageously, the processor device is adapted to determining a common mode signal as an average of the amplified electrophysiological signals, wherein the amplified electrophysiological signals are referenced with respect to the common mode signal. Further advantageously the differential amplifier stage is an average reference amplifier, wherein the average of the amplified electrophysiological signals is fed back as a signal reference to the input side of the differential amplifier stage so as to reference the amplified electrophysiological signals to the common mode signal. Thereby, the quality of the amplified and presented signals is further enhanced, which further magnifies the improvements of intracardiac radiofrequency ablation procedures performed using the system.

Yet further details of using an average reference amplifier in a particularly advantageous configuration adapted for recording intracardiac electrophysiological signals and the advantages achieved thereby, in particular the advantages achieved by including both intracardiac signals and an indifferent signal in the common mode signal reference, are disclosed in co-pending patent application PCT/EP2016/057783 to the inventors, which is hereby incorporated by reference.

According to a yet further aspect, a method of filtering an intracardiac electrophysiological signal is provided with advantageous embodiments as detailed in the claims and further as disclosed herein. Thereby, at least the analogue advantages are achieved as those already discussed in the context of embodiments for the switching device and corresponding recording apparatus.

A method of filtering an intracardiac electrophysiological signal using a switchable filter device comprises the steps of:
  passing the intracardiac electrophysiological signal through a first signal path with a first circuit configuration, wherein the first signal path has a first frequency dependent transmission characteristic with a first pass band;
  monitoring for a transient interference signal;
  upon occurrence of the transient interference signal, switching from the first signal path to a second signal path with a second circuit configuration, wherein the second signal path has a second frequency dependent transmission characteristic different from the first frequency dependent transmission characteristic, the second frequency dependent transmission characteristic having a second pass band overlapping the first pass band; and
  upon termination of the transient interference signal, switching from the second signal path to the first signal path;
wherein switching from the second signal path to the first signal path is performed with a switching delay after termination of the transient interference signal.

An intracardiac electrophysiological signal is received as unfiltered input at a patient side interface of the switchable filter device, processed through the filtering device, and then provided as filtered output at a recording side interface of the switchable filter device. Between the patient side interface and the recording side interface, the intracardiac electrophysiological signal is passed through a first signal path with a first circuit configuration, wherein the first signal path has a first frequency dependent transmission characteristic with a first pass band. Monitoring means are provided for monitoring for a transient interference signal and generating a control signal indicative of a status of the transient interference signal. As mentioned above, the status includes one or more of "absence", "occurrence", "presence", and "termination" of the transient interference signal. The control signal is received and employed to operate the switching devices. In response to the control signal indicating occurrence of the transient interference signal, the switching devices are operated to switch from the first signal path to a second signal path with a second circuit configuration. The second signal path has a second frequency dependent transmission characteristic different from the first frequency dependent transmission characteristic. Furthermore, the second frequency dependent transmission characteristic has a second pass band overlapping the first pass band. The intracardiac electrophysiological signal is thus routed through the second signal path where it is filtered according to the requirements imposed by the presence of strong interference. When the monitoring means detect termination of the transient interference signal a corresponding control signal is generated. In response to the control signal indicating termination of the transient interference signal, the switching means are operated to switch from the second signal path to the first signal path. Most preferably, switching from the circuit configuration of the second signal path to the circuit configuration of the first signal path is performed with a switching delay after termination of the transient interference signal as indicated by the control signal.

Further according to some embodiments of the method, switching from the first signal path to the second signal path occurs within 100 ms, preferably within 10 ms, or even more preferably within 1 ms after occurrence of the transient interference signal.

Further according to some embodiments of the method, the switching delay is at least 0.1 s, or at least 0.2 s, or at least 0.5 s, or at least 1 s, or at least 2 s, or at least 5 s.

Further according to some embodiments of the method, switching from the second signal path to the first signal path is performed via at least one stage during which a high pass filter of the second signal path is referenced to an unfiltered signal line, before entirely switching to the circuit configuration of the first signal path.

Preferably, at least a high pass filtering configuration is switched via at least one intermediate stage, during which the high pass filter of the second signal path is referenced to the unfiltered signal instead of being referenced to a common signal ground as during ablation. Upon expiry of the switching delay, the circuit configuration is switched entirely to the first signal path. Thereby, an offset of the filtered intracardiac electrophysiological signal is driven to the offset of the unfiltered intracardiac electrophysiological signal, i.e. the offset as observed directly without filtering at the patient side terminal of the respective recording channel, thus avoiding or at least substantially reducing any artefacts in the filtered intracardiac signals as may be observed at the recording side terminal of the respective recording channel, due to an abrupt switching of the high pass filter.

Further according to some embodiments of the method, switching from the second signal path to the first signal path is performed via at least two stages, before entirely switching to the circuit configuration of the first signal path, the stages comprising:
- an initial relaxation stage with a high pass filter of the second signal path being referenced to a common signal ground; and, after the relaxation stage,
- a signal referenced stage with the high pass filter of the second signal path referenced to the unfiltered signal.

Further according to some embodiments of the method, switching from the second signal path to the first signal path is performed via at least two stages, before entirely switching to the circuit configuration of the first signal path, the stages comprising:
- a primary signal referenced stage with a primary high pass filter configuration, where the high pass filter of the second signal path is referenced to the unfiltered signal; and, after the primary signal referenced stage,
- a secondary signal referenced stage with a secondary high pass filter configuration, wherein a secondary high pass filter replacing the primary high pass filter is referenced to the unfiltered signal, and wherein the secondary high pass filter has a low frequency cut-off above the low frequency cut-off of the primary high pass filter.

Further according to some embodiments of the method, the first pass-band is broader than the second pass band.

Further according to some embodiments of the method, a high frequency roll-off of the second frequency dependent transmission characteristic is steeper than a high frequency roll-off of the first frequency dependent transmission characteristic; and/or a low frequency roll-off of the second frequency dependent transmission characteristic is steeper than a low frequency roll-off of the first frequency dependent transmission characteristic.

Further according to some embodiments of the method, a low frequency cut-off is 0.5 Hz or below, preferably 0.1 Hz or below, or 0.05 Hz.

Further according to some embodiments of the method, a low frequency cut-off of the second signal path is above a low frequency cut-off of the first signal path.

Further according to some embodiments of the method, a low frequency cut-off of the second signal path is between 10 Hz and 50 Hz, or between 20 Hz and 40 Hz, or between 25 Hz and 35 Hz, or 30 Hz.

BRIEF DESCRIPTION OF THE DRAWINGS

Preferred embodiments of the invention will be described in more detail in connection with the appended drawings, which show schematically in FIG. 1 a switchable filtering device according to one embodiment.

DETAILED DESCRIPTION OF PREFERRED EMBODIMENTS

Figure 1:
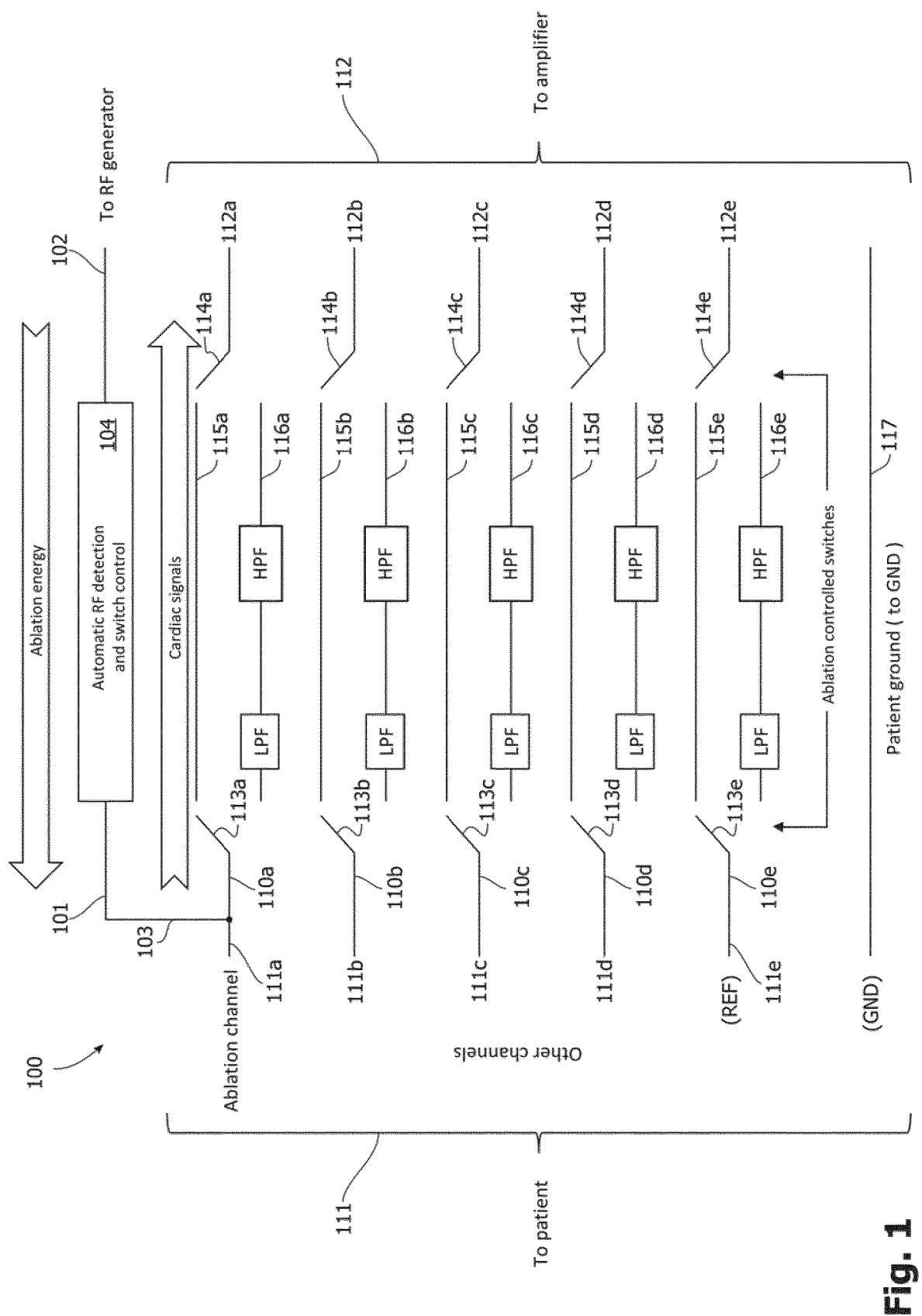

FIG. 1 shows schematically a switchable filtering device 100 for use in a system for recording intracardiac electrophysiological signals and for providing radiofrequency ablation energy at intracardiac locations according to one embodiment. The switchable filter device 100 comprises a plurality of recording channels 110a-e. Each recording channel 110a-e has a patient side terminal 111a-e at a patient interface 111 and a corresponding recording side terminal 112a-e at a recording device interface 112.

The plurality of recording channels includes an ablation recording channel 110a, which differs from the other channels 110b-e in that the patient side terminal 111a of the ablation recording channel 110a is connected to an ablation input channel 101. The ablation input channel 101 has an ablation input terminal 102 and an ablation output terminal 103, wherein the ablation input channel 101 is configured for transmitting a radiofrequency ablation signal from the ablation input terminal 102 to the ablation output terminal 103 as indicated by the arrow labelled "Ablation energy". The ablation output terminal 103 of the ablation channel 101 is connected at the patient interface 111 to the patient side terminal 111a of the ablation recording channel 110a for delivering the radiofrequency ablation signal through said patient side terminal 111a via the ablation channel of an ablation catheter, such as the multi-electrode catheter 3 schematically shown in FIG. 4, to an ablation site in the patient's heart. The ablation input channel 101 comprises a radiofrequency detection device 104 configured for providing a radiofrequency detection output in response to the presence of a radiofrequency ablation signal in the ablation input channel 101.

Each of the recording channels 110a-e comprises a respective first signal path 115a-e with a frequency dependent transmission characteristic having a first pass band, a respective second signal path 116a-e with a second frequency dependent transmission characteristic having a second pass band overlapping the first pass band, which is more narrow than the first pass band and/or having steeper roll-offs than the first frequency dependent transmission characteristic, and respective switching devices 113a-e, 114a-e that are operable to switch between the first signal path 115a-e and the second signal path 116a-e in response to the radiofrequency detection output of the radiofrequency detection device 104. Thereby, the switching devices 113a-e, 114a-e are ablation controlled to choose the first signal path 115a-e or the second signal path 116a-e depending on whether a radiofrequency ablation signal is absent or present, respectively. The second pass band of the second signal paths 116a-e has a low frequency cut-off and a high-frequency cut-off as indicated by high pass filter elements HPF and low pass filter elements LPF. The respective first signal paths 115a-e may be configured as simple transmission lines. Switching between the first signals paths 115a-e and second signal paths 116a-e then essentially amounts to switching the aggressive ablation filtering of the second signal paths 116a-e ON and OFF.

Preferably, the filter configurations are nominally identical in all recording channels 110a-e, apart from variations due to component tolerances. A nominally identical filter configuration in all recording channels 110a-e allows for combining the signals of different recording channels, for example in order to achieve an efficient common mode noise reduction, e.g. using an average reference amplifier as described in the above-mentioned international patent application PCT/EP2016/057783. Further preferably, the switching devices 113a-e, 114a-e of the recording channels 110a-e are configured for synchronous operation in response to the radiofrequency detection output provided by the radiofrequency detection device 104.

One of the recording channels, here recording channel 110e, is typically connected to an indifferent electrode on or in the patient for providing a reliable electrophysiological reference (REF) against which the intracardiac electrophysiological signals collected at any of the remaining recording channels 110a-d may be referred in order to provide unipolar signals that are improved in terms of common mode rejection as well as morphology in order to be most useful for diagnostic purposes.

The switchable filtering device 100 shown schematically in FIG. 1 further comprises a common ground (GND) terminal 117, which at the patient interface may be connected to a patient ground terminal to provide a common ground (GND) to which the circuits of the switchable filtering device 100 may be tied. The common ground terminal 117 may further be connected the recording interface 112 to also provide the common ground (GND) as a circuit reference to subsequent amplification and recording devices, such as amplifier 40 and processor 50 shown schematically in FIG. 4. As in a typical electrophysiology set-up, the patient ground (GND) is electrically isolated from earth ground.

Figure 2:
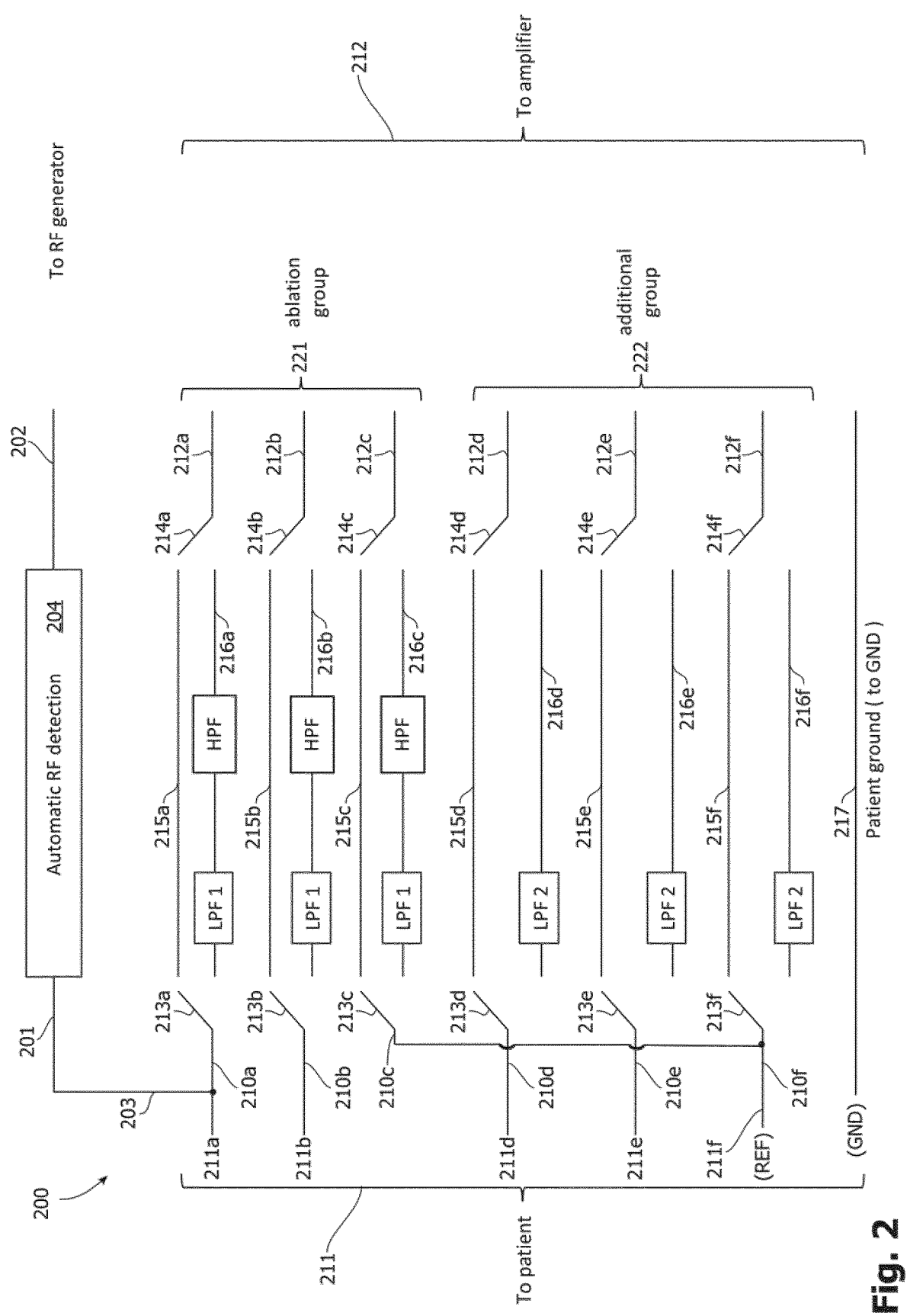
FIG. 2 a switchable filtering device according to another embodiment.

FIG. 2 shows schematically a switchable filtering device 200 for use in a system for recording intracardiac electrophysiological signals and for providing radiofrequency ablation energy at intracardiac locations according to another embodiment. The switchable filter device 200 comprises a plurality of recording channels 210a-f. Each recording channel 210a-f has a respective patient side terminal 211a-f at a patient interface 211 and a corresponding recording side terminal 212a-f at a recording device interface 212.

The plurality of recording channels includes an ablation recording channel 210a, which differs from the other channels 210b-f in that the patient side terminal 211a of the ablation recording channel 210a is connected to an ablation input channel 201. The ablation input channel 201 has an ablation input terminal 202 and an ablation output terminal 203, wherein the ablation input channel 201 is configured for transmitting a radiofrequency ablation signal from the ablation input terminal 202 to the ablation output terminal 203. The ablation output terminal 203 of the ablation channel 201 is connected at the patient interface 211 to the patient side terminal 211a of the ablation recording channel 210a for delivering the radiofrequency ablation signal through said patient side terminal 211a via the ablation channel of an ablation catheter, such as the multi-electrode catheter 3 schematically shown in FIG. 4, to an ablation site in the patient's heart. The ablation input channel 201 comprises a radiofrequency detection device 204 configured for providing a radiofrequency detection output in response to the presence of a radiofrequency ablation signal in the ablation input channel 201.

Each of the recording channels 210a-f comprises a respective first signal path 215a-f with a frequency dependent transmission characteristic having a first pass band, a respective second signal path 216a-f with a second frequency dependent transmission characteristic having a second pass band overlapping the first pass band, which is more narrow than the first pass band and/or having steeper roll-offs than the first frequency dependent transmission characteristic, and respective switching devices 213a-f, 214a-f that are operable to switch between the first signal path 215a-f and the second signal path 216a-f in response to the radiofrequency detection output of the radiofrequency detection device 204. Thereby, the switching devices 213a-f, 214a-f are ablation controlled to choose the first signal path 215a-f or the second signal path 216a-f depending on whether a radiofrequency ablation signal is absent or present, respectively. The second pass band of the second signal paths 216a-f has a low frequency cut-off and a high-frequency cut-off as indicated by high pass filter elements HPF and low pass filter elements LPF1, LPF2. The respective first signal paths 215a-f may be configured as simple transmission lines. Switching between the first signals paths 215a-f and second signal paths 216a-f then essentially amounts to switching the aggressive ablation filtering of the second signal paths 216a-f ON and OFF.

The embodiment of FIG. 2 differs from the embodiment of FIG. 1 in that subsets of the recording channels 210a-f are grouped together to comprise two groups, namely an ablation group 221, and an additional group 222. The ablation group 221 comprises the ablation recording channel 210a, and two further recording channels 210b-c, and the additional group comprises the remaining recording channels not including an ablation channel. Since the additional group does not include a recording channel that is connected to an ablating electrode during radiofrequency catheter ablation, the recording channels receive electrophysiological signals with a somewhat different electrophysiological noise and artefact environment and may, even during ablation, suffer significantly less base line drift and may be less sensitive to the radiofrequency ablation signal transmitted. The recording channels 210d-f of the additional group 222 may therefore, as shown here, even omit the high pass filters in the second signal paths 116d-f and may further be fitted with low pass filters LPF2 that are different from the low pass filters LPF1 of the recording channels 210a-c of the ablation group 221.

The ablation group 221 and any additional groups 222 are typically independent of each other, except for the case of a shared electrophysiological reference as described in the following. Preferably, within a given group 221, 222, the filter configurations are nominally identical in all recording channels 210a-c, 210d-f within that given group 221, 222, apart from variations due to component tolerances. A nominally identical filter configuration in all recording channels 210a-c, 210d-f allows for easily combining and processing the filtered electrophysiological signals stemming from the same group. For example, in the ablation group 221, signals collected from an ablation electrode and filtered through the ablation recording channel 210a may be combined with signals collected from an adjacent intracardiac electrode and filtered through a further recording channel 210b to obtain a bipolar intracardiac electrophysiological signal. Alternatively, in the ablation group 221, signals collected from an ablation electrode and filtered through the ablation recording channel 210a may be combined with signals collected from an indifferent electrode arrangement and filtered through a yet further recording channel 210c to obtain a unipolar intracardiac electrophysiological signal referred to an electrophysiological reference on or in the patient.

Requiring the same filter configuration for all recording channels 210a-c, 210d-f within a given group 221, 222 also facilitates efficient common mode noise suppression. In particular, if the additional group 221 comprises a multitude of recording channels 210d-f, such as three, four, five, six, seven, eight, or more recording channels, an efficient common mode noise reduction may be achieved, for example by using an average reference amplifier as described in the above-mentioned international patent application PCT/EP2016/057783.

Further preferably, operation of the switching devices 213a-f, 214a-f of the recording channels 210a-f in response to the radiofrequency detection output provided by the radiofrequency detection device 204 is synchronized at least within a given group 221, 222 of recording channels 210a-c, 210d-f. When different filter configurations are used in the ablation and additional groups, the switch operation may also differ between the groups. For example, if high pass filters HPF are present in the ablation group, but absent from the additional group, a switch-off delay may be applied for switching from the second to the first signal path in the ablation group 221, but not in the additional group 222.

One of the recording channels in each group 221, 222, here recording channels 210c and 210f, respectively, is typically connected to an indifferent electrode on or in the patient for providing a reliable electrophysiological reference (REF) against which the intracardiac electrophysiological signals collected at the remaining recording channels 210a-b and 210d-e, respectively, may be referred to obtain signals that are improved in terms of common mode rejection as well as in terms of their morphology, in order to be most useful for diagnostic purposes. Most preferably, as shown in FIG. 2, the electrophysiological reference (REF) is received at the patient interface 211 at a single terminal, and then shared between the recording channel groups 221, 222, e.g. via an optional buffer.

The switchable filtering device 200 shown schematically in FIG. 2 further comprises a common ground (GND) terminal 217, which at the patient interface may be connected to a patient ground terminal to provide a common ground (GND) to which the circuits of the switchable filtering device 200 may be tied. The common ground terminal 217 may further be connected to the recording interface 212 to also provide the common ground (GND) as a circuit reference to subsequent amplification and recording devices, such as amplifier 40 and processor 50 shown schematically in FIG. 4. As in a typical electrophysiology set-up, the patient ground (GND) is electrically isolated from earth ground.

Figure 3:
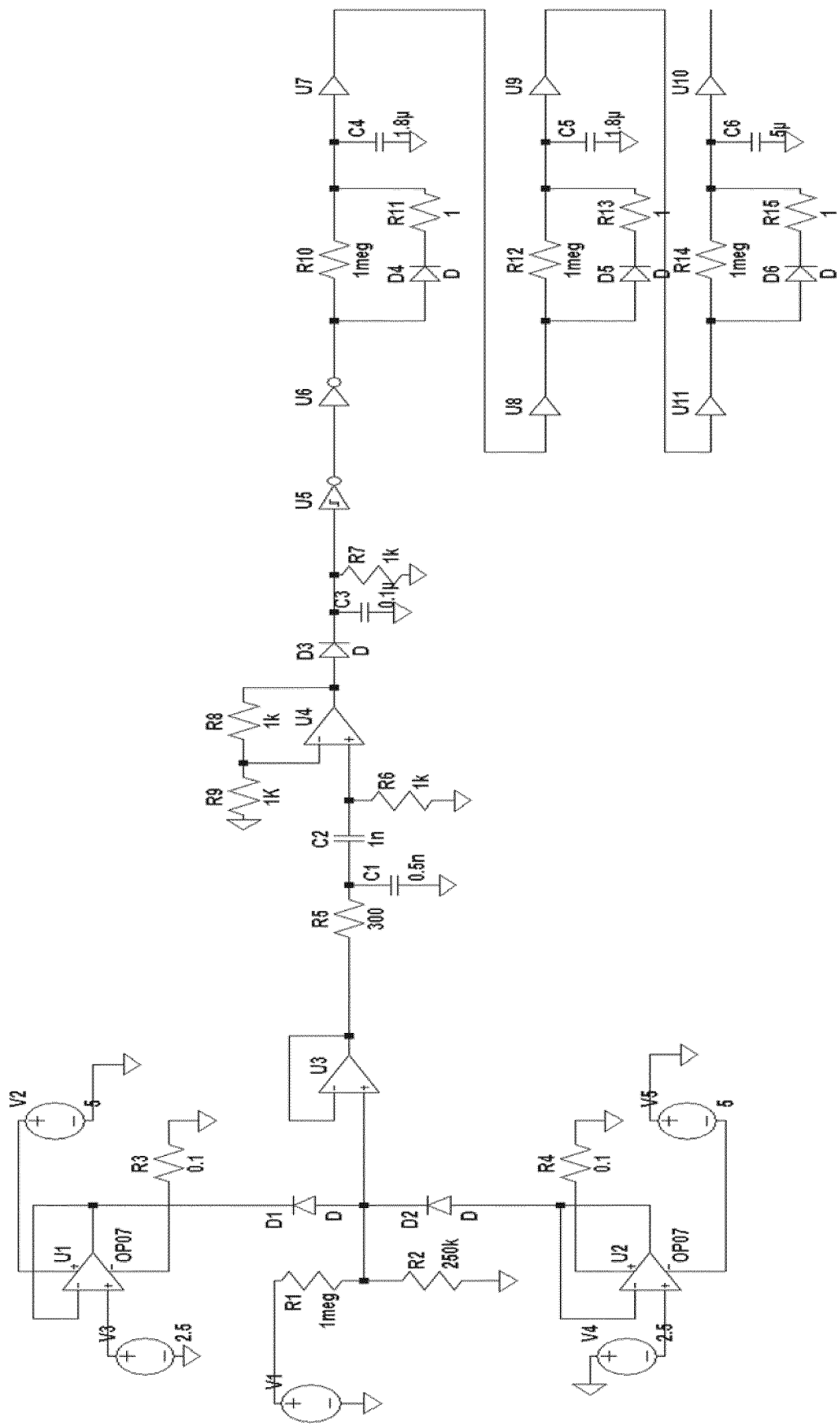
FIG. 3 an automatic ablation detection device according to one embodiment.

FIG. 3 shows, by way of example, an ablation detection circuit 300 for use in the automatic radiofrequency detection devices 104, 204. FIG. 3 shows schematically the circuit used for detection of the presence of a radiofrequency ablation signal and for signaling this information to filter switches. In the schematic, the radiofrequency ablation signal is represented by V1 on the left-hand-side. The radiofrequency ablation signal goes partly to the patient (not shown) and partly through a voltage divider and further through the detection circuit. The detection circuit ties into the radiofrequency ablation signal through a 1MΩ resistor. This is used in combination with a 250KΩ resistor in order to create a 1/5 division. In this case, a minimal 15V signal is divided down to 3V. The 1MΩ resistor limits the current drawn during ablation performed with 320V, to less than 0.32 mA. D1 and D2 are diodes that clamp the radiofrequency signal to +/−3.2 V, and these are followed by a unity gain buffer (U3). The radiofrequency signal passes through a Low Pass Filter tuned for a corner frequency of 1 MHz using a 300Ω resistor and a 500 pF capacitor. The signal then passes through a High Pass Filter tuned for 160 KHz using a 1 nF capacitor and a 1KΩ resistor. After filtering, the signal is buffered and amplified with a gain of 2 by a second operational amplifier (U4). The buffered signal passes through a half-wave rectifier (D3). The rectified signal charges a 0.1 uF capacitor which is drained by a 1KΩ resistor. A non-inverting Schmitt trigger (U5) is used to generate a pure digital signal. This digital signal enters into a circuit intended to quickly charge a capacitor and slowly discharge it in three stages so as to provide minimal delay after the start of an ablation signal and a switch-off delay after the termination of a radiofrequency ablation signal.

During ablation the unfiltered electrophysiological signals are drifting to higher (positive or negative) DC offset. The filtered electrophysiological signals are kept within the dynamic range of a subsequent amplifying and/or signal processing stage by means of the high pass filters of the second filter paths. After ablation has terminated, it will take some time before the unfiltered electrophysiological signals are back in range, which is why the control signal for switching the signal paths back to the first signal path is kept delayed. However, even when the unfiltered signal is back within the dynamic range of the subsequent stages, there will still be an abrupt DC jump to the natural offset, if the high pass filters HPF are switched off abruptly. Instead, the high pass filters HPF preferably go through one or more intermediate stages, such as three stages after termination of the radiofrequency ablation signal has been detected. For example, the following program may be applied during a total switch-off delay of 5 seconds:

Stage 0, Ablation on: 0.05 Hz high pass filter tied to GND (drives the signal to 0);
Stage I, 0-1 second after ablation termination: 0.05 Hz high pass filter tied to GND (optional, same as stage 0);
Stage II, 1-2 seconds after ablation termination: 0.05 Hz filter tied to the unfiltered electrophysiological signal (drives the signal to the offset of the unfiltered signal);
Stage III, 2-5 seconds after ablation termination: 0.3 Hz filter tied to un-filtered signal (optional, drives the signal faster to the offset of the unfiltered signal than stage II);

When filters are tied to the un-filtered signal, the signals are driven slowly to the natural offset of the unfiltered signal instead the abrupt jump that would happen if the filters were just switched off after stage I.

Figure 4:
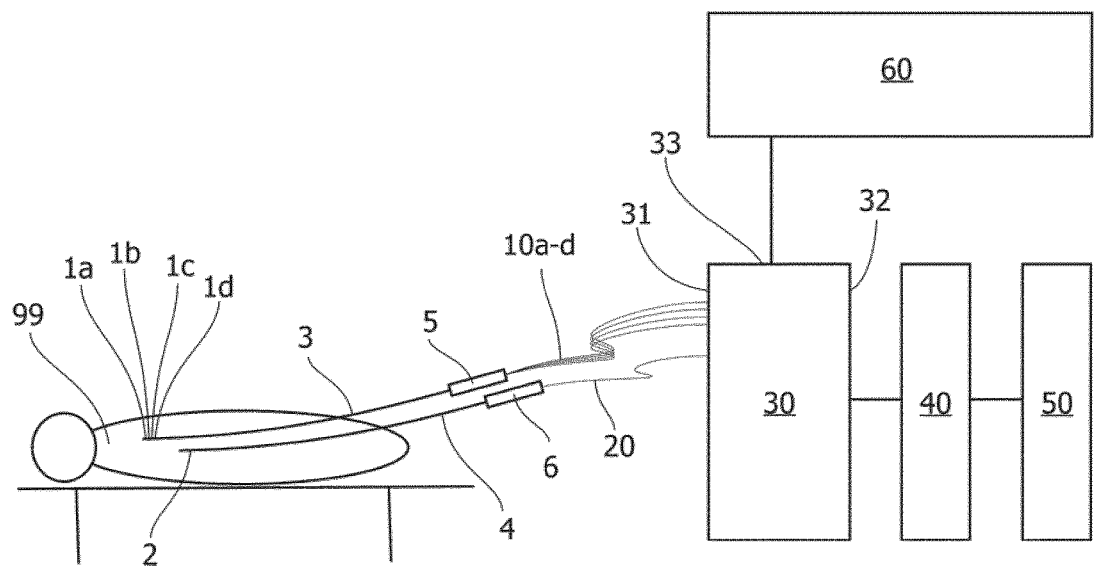
FIG. 4 a system for recording intracardiac signals and for providing radiofrequency ablation energy at intracardiac locations.

FIG. 4 shows schematically a set-up including a system for recording intracardiac signals and for providing radiofrequency ablation energy at intracardiac locations of an individual 99 according to one embodiment of the invention.

The system comprises a plurality of patient side terminals 10a-d at a patient interface 31 of the switchable filtering device 30. The patient side terminals 10a-d are connected to respective intracardiac electrodes 1a-d at the distal end of a multi-electrode catheter 3 via an interface 5 at the proximal end of the catheter 3. The intracardiac electrodes 1a-d comprise an ablation electrode 1a configured for radiofrequency ablation using a radiofrequency ablation signal delivered through a patient side terminal 10a of the system. The system further comprises an indifferent terminal 20 that is connected to an indifferent electrode 2 in the patient 99. Alternatively, an indifferent electrode arrangement may be placed on the surface of the body of the patient 99. An indifferent electrode 2 in the patient 99 may be connected to an intra-cardiovascular indifferent electrode 2 at the distal end of a catheter 4 via an interface 6 at the proximal end of the catheter 4. Alternatively, the indifferent electrode 2 in the patient can be located on a sheath used for guiding the multi-electrode catheter 3. The indifferent electrode 2 is for providing an electrophysiological reference from the patient to the system. The electrophysiological signals received by the patient side terminals 10a-d, 20 are filtered and, via recording side terminals at the recording interface 32 of the switchable filter device 30, passed to a differential amplifier stage 40 where they are amplified with respect to a signal reference. The amplified electrophysiological signals obtained from the amplifier stage 40 are passed to a processor device 50. The processor device 50 generates an output of intracardiac data at an output interface. The intracardiac data output is based at least on the intracardiac electrophysiological signals, wherein the intracardiac signals may advantageously be referenced with respect to the common mode signal. A radiofrequency ablation signal is generated by an ablation generator 60 and passed to the ablation input terminal 33 of the switchable filtering device 30.

A typical set-up may include further apparatus, such as for 3D mapping catheter probes, for monitoring the individual, for stimulation of the heart, and/or for applying defibrillation. Such further apparatus has been omitted in FIG. 4 for reasons of clarity. The system further comprises a differential amplifier stage 40 and a processor device 50 communicating with each other via a link.

Prior to recording, the electrodes 1a-d have been placed in an intracardiac location in a known manner, e.g. in a minimally invasive procedure by means of a catheter 3 carrying the plurality of electrodes 1a-d. The intracardiac electrodes are located within the same heart chamber to be monitored and probe the intracardiac electrophysiological potentials at their respective intracardiac locations. Furthermore, the electrode 2 has been placed in an intra-cardiovascular location, e.g. in the inferior vena cava, by means of a catheter 4, and probes electrophysiological potentials that are considered indifferent with respect to the intracardiac electrophysiological potentials. As mentioned above, the indifferent electrode 2 in the patient may also be located on a sheath used for guiding the multi-electrode catheter 3. Alternatively, the indifferent electrode may be placed on the surface of the body using a surface electrode. The indifferent electrode 2 is for providing an electrophysiological reference from the patient to the system. The probed electrophysiological potentials from the electrodes 1a-d, and 2 are transmitted to the interfaces 5, 6 at the proximal end of the catheters 3, 4 via respective leads. Advantageously, the intracardiac electrodes 1a-d and their respective leads are bundled in a single catheter 3, whereas the indifferent electrode 2 is placed on a separate catheter 4. However, different bundling combinations may be conceived, e.g. a set-up where the intracardiac electrodes 1a-d and the indifferent electrode 2 are grouped on one catheter, or a set-up comprising multiple catheters comprising multiple groups of intracardiac electrodes for simultaneously probing intracardiac potentials at respective locations. Furthermore, the number of four intracardiac electrodes shown in FIG. 4 is to be considered as an example and different numbers of intracardiac electrodes, such as 5, 6, 7, 8, 9, 10, 20, 50, 100, or even more may be conceived. The intracardiac potentials from the intracardiac electrodes 1a-d are collected at interface 5 by the respective intracardiac terminals 10a-d. Accordingly, the indifferent potential from the indifferent electrode 2 is collected at interface 6 by the indifferent terminal 20. While the indifferent potential provided at the interface 6 in the set-up shown in FIG. 4 is defined by a single electrode 2, it may also be conceived that the indifferent potential collected by the indifferent terminal 20 is defined as a combination of potentials probed by a plurality of electrodes.

Preferably, the signal reference is common for all amplifier channels. In a particularly advantageous embodiment, the amplifier stage has an average reference amplifier configuration, wherein the average of all amplifier output signals is fed back to the input side of the amplifier stage and is used as the signal reference. Thereby a good first level suppression of mains interference as common mode noise is achieved already in the differential amplifier stage. Alternatively, the amplifier stage has a common reference amplifier configuration, wherein an indifferent potential may be used as common reference for all amplifier channels.

Figure 5:
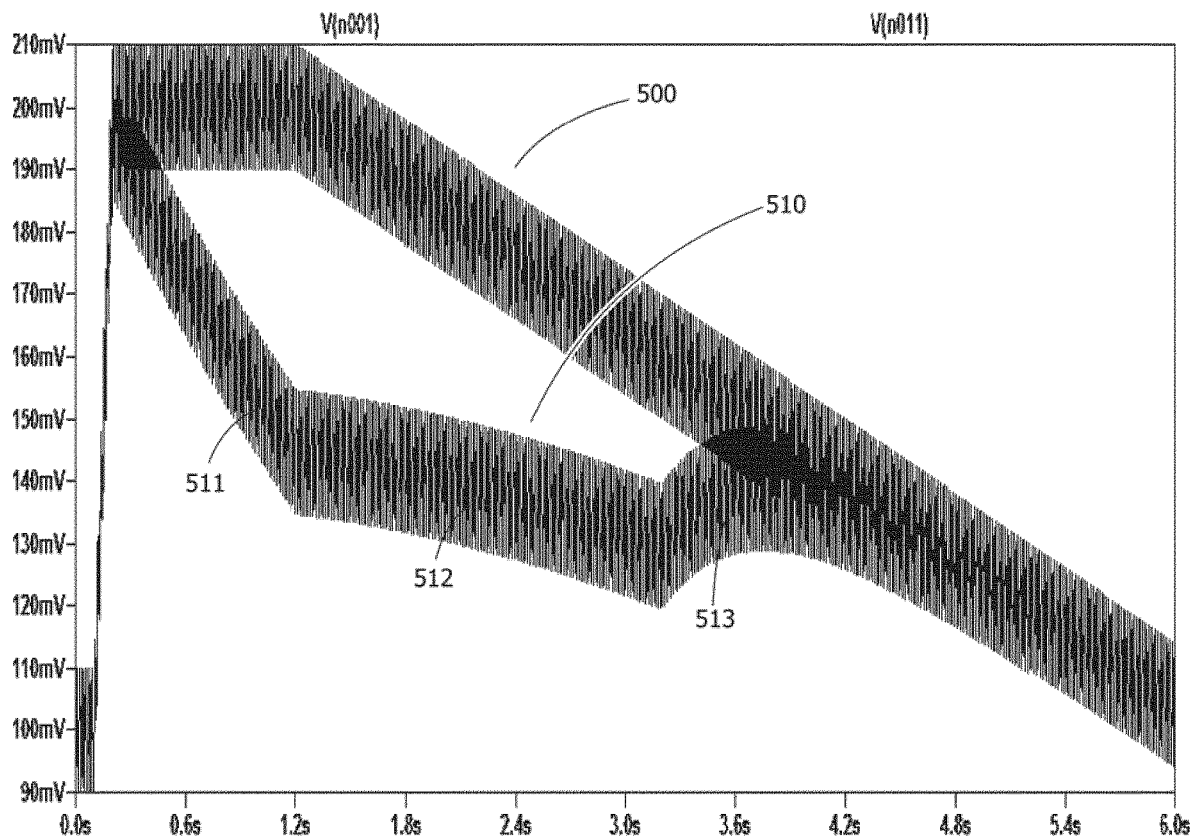
FIG. 5 a simulation of unfiltered and filtered signals when switching off high pass filtering upon termination of radiofrequency ablation via intermediate stages.

FIG. 5 illustrates, by way of a simulation example, the signal path switching in multiple stages after termination of the radiofrequency ablation signal has been detected. The graph shown in FIG. 5 shows the baseline changes for a simulated unfiltered signal 500, and in comparison thereto, the corresponding baseline changes for filtered signal 510 as a function of time after termination of the radiofrequency ablation signal at t=1.2 s. It is estimated that the signal of interest will have a 100 mV offset at all times, and during ablation the DC offset increases to 200 mV. The unfiltered signal 500 is thus shown to rise to an offset of 200 mV, which slowly decreases after termination of the ablation signal. The filtered signal 510 goes through three stages 511, 512, 513 of filtering circuit configurations. In all cases a 33 uF capacitor is kept in the signal path. The control signals from the ablation detection circuit are used to control analog switches, which in turn connect the appropriate sized resistor to the appropriate reference point.

The filtered signal thus evolves as follows:
  0.2 s: Ablation starts with a high pass filter with 0.05 Hz low frequency cut-off tied to isolated circuit ground (GND) switched on (switch from first signal path to second signal path); Here, the ADG1636 switch connects a 100 KOhm resistor to isolated circuit ground;
  1.2 s: Ablation stops and with 0.05 Hz low frequency cut-off is switched from being tied to common ground (GND) to being tied to the unfiltered signal; Here a second ADG1636 switch connects a 100 KOhm resistor to the output of the non-filtered signal path buffer
  3.2 s: The low-frequency cut-off is switched from 0.05 Hz to 0.3 Hz, the high pass filter is maintained tied to the unfiltered signal; Here a third ADG1636 switch connects a 15 KOhm resistor to the output of the non-filtered signal path buffer;
  6.2 s: All filters are switched off (back to first signal path).

Thereby, after termination of the ablation, the offset of the filtered signal 510 is brought as close as possible to the offset of the unfiltered signal 500, before fully switching the high pass filters off. This is performed more slowly in the start to avoid switching artefacts before the unfiltered signal has come back to within the dynamic range of the subsequent amplifier/processing circuit. Once within range, the process is accelerated by switching to a higher low-frequency cut-off before switching fully to the circuit configuration of the first signal path.

Figure 6A:
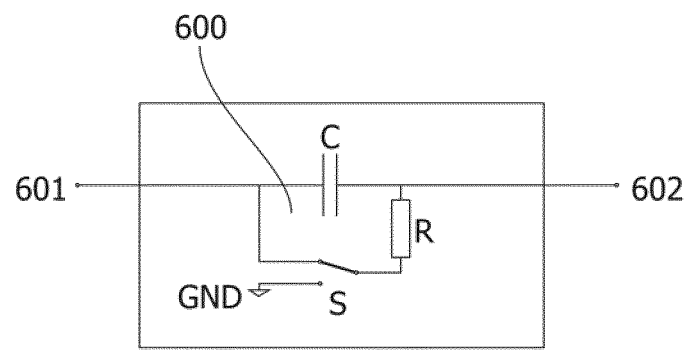
FIG. 6a,b two circuit configurations representing respective signal paths in a recording channel of a switchable filtering device according to one embodiment; and in FIG. 7 a sequence of switching between different signal paths in response to a control signal.
Figure 6B:
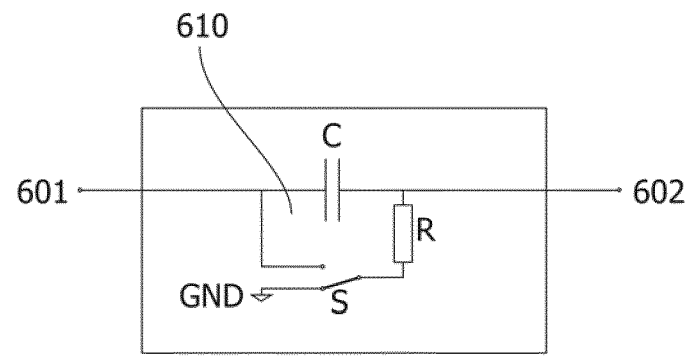

FIG. 6a and FIG. 6b show schematically a recording channel of a switchable filter device according to one embodiment with a high pass filter as indicated by capacitor C and resistance R. The recording channel has a patient side terminal 601 and a recording side terminal 602. The circuit configuration of the recording channel is switchable by switching means S (in response to a control signal not shown here). FIG. 6a shows a first circuit configuration 600 defining a first signal path, where the high pass filter is referenced to the unfiltered signal at terminal 601. FIG. 6b shows a second circuit configuration 610 defining a second signal path, where the high pass filter is referenced to a common ground terminal GND.

Figure 7:
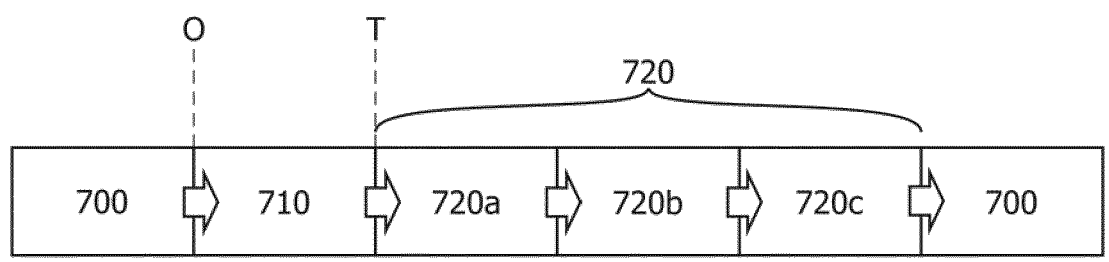

FIG. 7 shows a schematic of a switching sequence in a filtering method according to one embodiment of the invention. In the order of the sequence as indicated by the arrows, an electrophysiological signal is passed through a first signal path with a first circuit configuration 700. By monitoring for a transient interference signal, the occurrence of a transient interference signal is determined and indicated by a corresponding control signal status "0". Upon occurrence "0" of the transient interference signal as indicated by the control signal, switching from the first signal path 700 to a second signal path with a second circuit configuration 710 is immediately performed. Further monitoring for the transient interference signal, the termination of the transient interference signal is determined and indicated by a corresponding control signal status "T". After termination "T" of the transient interference signal as indicated by the control signal, switching from the second signal path 710 back to the first signal path 700 is performed with a switching delay 720 after termination "T" of the transient interference signal. Switching from the second signal path 710 to the first signal path 700 may be performed via multiple intermediate stages 720a-c as already discussed in detail above.

The invention claimed is:

1. A switchable filter device for use in a system for recording intracardiac electrophysiological signals at intracardiac locations, the filter device comprising:
a plurality of recording channels, the recording channels comprising at least one ablation recording channel, wherein each recording channel has a patient side terminal at a patient interface and a corresponding recording side terminal at a recording device interface; wherein
the filter device further comprises a detection device configured for monitoring for a transient interference signal and providing a control signal indicative of a status of the transient interference signal; and
each recording channel comprises a first signal path with a first frequency dependent transmission characteristic having a first pass band, a second signal path with a second frequency dependent transmission characteristic different from the first frequency dependent transmission characteristic, the second frequency dependent transmission characteristic having a second pass band overlapping the first pass band, and switching devices operable to switch between the first signal path and the second signal path in response to the control signal, wherein switching from the circuit configuration of the second signal path to the circuit configuration of the first signal path is performed with a switching delay.

2. The switchable filter device according to claim 1, wherein the first pass-band is broader than the second pass band.

3. The switchable filter device according to claim 1, wherein a high frequency roll-off of the second frequency dependent transmission characteristic is steeper than a high frequency roll-off of the first frequency dependent transmission characteristic; and/or wherein a low frequency roll-off of the second frequency dependent transmission characteristic is steeper than a low frequency roll-off of the first frequency dependent transmission characteristic.

4. The switchable filter device according to claim 1, wherein frequency cut-off is 0.5 Hz or below, 0.1 Hz or below, or 0.05 Hz.

5. The switchable filter device according to claim 1, wherein the switching delay is at least 0.1 s, or at least 0.2 s, or at least 0.5 s, or at least 1 s, or at least 2 s, or at least 5 s.

6. The switchable filter device according to claim 1, wherein switching from the second signal path to the first signal path is performed via at least one stage during which a high pass filter of the second signal path is referenced to an unfiltered signal line, before entirely switching to the circuit configuration of the first signal path.

7. The switchable filter device according to claim 1, wherein switching from the second signal path to the first signal path is performed via at least two stages, before entirely switching to the circuit configuration of the first signal path, the stages comprising:
an initial relaxation stage with a high pass filter of the second signal path being referenced to a common signal ground; and, after the relaxation stage, a signal referenced stage with the high pass filter of the second signal path referenced to the unfiltered signal.

8. The switchable filter device according to claim 1, wherein switching from the second signal path to the first signal path is performed via at least two stages, before entirely switching to the circuit configuration of the first signal path, the stages comprising:
a primary signal referenced stage with a primary high pass filter configuration, where the high pass filter of the second signal path is referenced to the unfiltered signal; and, after the primary signal referenced stage,
a secondary signal referenced stage with a secondary high pass filter configuration, wherein a secondary high pass filter replacing the primary high pass filter is referenced to the unfiltered signal, and wherein the secondary high pass filter has a low frequency cut-off above the low frequency cut-off of the primary high pass filter.

9. The switchable filter device according to claim 1, wherein an additional subset of the plurality of recording channels is grouped together to form an additional group, the additional group comprising at least two recording channels.

10. A system for recording intracardiac signals and for providing radiofrequency ablation energy at intracardiac locations, the system comprising:
the switchable filter device according to claim 1;
a radiofrequency ablation device coupled to the switchable filter device for feeding a radiofrequency ablation signal to the radiofrequency detection de-vice;
a differential amplifier stage coupled to the recording device interface of the switchable filter device for collecting the filtered electrophysiological signals from the recording channels, the differential amplifier stage being adapted to amplifying the filtered electrophysiological signals from the recording channels with respect to a signal reference to obtain respective amplified electrophysiological signals; and a processor device adapted to providing an output of intracardiac data based on the amplified electrophysiological signals.

11. The system according to claim 10, wherein the switchable filtering device of the system has recording channels that are grouped into an ablation group and an additional group.

12. The switchable filter device according to claim 1, wherein the detection device is configured for receiving a radiofrequency ablation signal and providing a radiofrequency detection output in response to the presence of a radiofrequency ablation signal, and wherein the switching devices are operable to switch between the first signal path and the second signal path in response to the radio frequency detection output.

13. The switchable filter device according to claim 12, wherein switching from the first signal path to the second signal path occurs within 100 ms, or within 10 ms, or within 1 ms after start of a radiofrequency ablation cycle for providing radiofrequency ablation energy at an intracardiac location.

14. The switchable filter device according to claim 12, wherein a subset of the plurality of recording channels is grouped together to form at least an ablation group, the ablation group comprising the at least one ablation recording channel and a further recording channel.

15. A method of filtering an electrophysiological signal using a switchable filter device, the method comprising the steps of:
passing the electrophysiological signal through a first signal path with a first circuit configuration, wherein the first signal path has a first frequency dependent transmission characteristic with a first pass band;
monitoring for a transient interference signal;
upon occurrence of the transient interference signal, switching from the first signal path to a second signal path with a second circuit configuration, wherein the second signal path has a second frequency dependent transmission characteristic different from the first frequency dependent transmission characteristic, the second frequency dependent transmission characteristic having a second pass band overlapping the first pass band; and upon termination of the transient interference signal, switching from the second signal path to the first signal path;
wherein switching from the second signal path to the first signal path is performed with a switching delay after termination of the transient interference signal.

16. The method according to claim 15, wherein switching from the first signal path to the second signal path occurs within 100 ms, within 10 ms, or within 1 ms after occurrence of the transient interference signal.

17. The method according to claim 15, wherein the switching delay is at least 0.1 s, or at least 0.2 s, or at least 0.5 s, or at least 1 s, or at least 2 s, or at least 5 s.

18. The method according to claim 15, wherein switching from the second signal path to the first signal path is performed via at least one stage during which a high pass filter of the second signal path is referenced to an unfiltered signal line, before entirely switching to the first signal path.

19. The method according to claim 15, wherein switching from the second signal path to the first signal path is performed via at least two stages, before entirely switching to the first signal path, the stages comprising:
an initial relaxation stage with a high pass filter of the second signal path being referenced to a common signal ground; and, after the relaxation stage, a signal referenced stage with the high pass filter of the second signal path referenced to the unfiltered signal.

20. The method according to claim 15, wherein switching from the second signal path to the first signal path is performed via at least two stages, before entirely switching to the first signal path, the stages comprising:
a primary signal referenced stage with a primary high pass filter configuration, where the high pass filter of the second signal path is referenced to the unfiltered signal; and, after the primary signal referenced stage,
a secondary signal referenced stage with a secondary high pass filter configuration, wherein a secondary high pass filter replacing the primary high pass filter is referenced to the unfiltered signal, and wherein the secondary high pass filter has a low frequency cut-off above the low frequency cut-off of the primary high pass filter.

21. The method according to claim 15, wherein the first pass-band is broader than the second pass band.

22. The method according to claim 15, wherein a high frequency roll-off of the second frequency dependent transmission characteristic is steeper than a high frequency roll-off of the first frequency dependent transmission characteristic; and/or wherein a low frequency roll-off of the second frequency dependent transmission characteristic is steeper than a low frequency roll-off of the first frequency dependent transmission characteristic.

23. The method according to claim 15, wherein a low frequency cut-off of the first signal path is 0.5 Hz or below, 0.1 Hz or below, or 0.05 Hz.

24. The method according to claim 15, wherein a low frequency cut-off of the second signal path is above a low frequency cut-off of the first signal path.

25. The method according to claim 15, wherein a low frequency cut-off of the second signal path is between 10 Hz and 50 Hz, or between 20 Hz and 40 Hz, or between 25 Hz and 35 Hz, or 30 Hz.

* * * * *